(12) United States Patent
Chuang et al.

(10) Patent No.: US 9,529,182 B2
(45) Date of Patent: Dec. 27, 2016

(54) 193NM LASER AND INSPECTION SYSTEM

(71) Applicant: KLA-Tencor Corporation, Milpitas, CA (US)

(72) Inventors: Yung-Ho Chuang, Cupertino, CA (US); J. Joseph Armstrong, Fremont, CA (US); Yujun Deng, San Jose, CA (US); Justin Dianhuan Liou, Santa Clara, CA (US); Vladimir Dribinski, Livermore, CA (US); John Fielden, Los Altos, CA (US)

(73) Assignee: KLA—Tencor Corporation, Milpitas, CA (US)

( * ) Notice: Subject to any disclaimer, the term of this patent is extended or adjusted under 35 U.S.C. 154(b) by 187 days.

(21) Appl. No.: 14/170,384

(22) Filed: Jan. 31, 2014

(65) Prior Publication Data
US 2014/0226140 A1 Aug. 14, 2014

Related U.S. Application Data

(60) Provisional application No. 61/764,441, filed on Feb. 13, 2013.

(51) Int. Cl.
*G01N 21/95* (2006.01)
*H01S 3/00* (2006.01)
(Continued)

(52) U.S. Cl.
CPC ....... *G02B 17/0892* (2013.01); *G01N 21/9501* (2013.01); *H01S 3/0092* (2013.01); *H01S 3/2308* (2013.01)

(58) Field of Classification Search
CPC ............ G01N 21/9501; G02B 17/0892; H01S 3/0092; H01S 3/2308
See application file for complete search history.

(56) References Cited

U.S. PATENT DOCUMENTS

| | | | |
|---|---|---|---|
| 3,755,704 A | 8/1973 | Spindt et al. | |
| 4,178,561 A | 12/1979 | Hon et al. | |

(Continued)

FOREIGN PATENT DOCUMENTS

| | | |
|---|---|---|
| CN | 101702490 | 5/2010 |
| DE | 102007004235 | 1/2008 |

(Continued)

OTHER PUBLICATIONS

KLA-Tencor Corporation; PCT International Search Report dated Dec. 29, 2015 for Application No. PCT/US2015/051538, 3 pages.

(Continued)

*Primary Examiner* — Mark R Gaworecki
(74) *Attorney, Agent, or Firm* — Bever, Hoffman & Harms, LLP

(57) ABSTRACT

An improved solid-state laser for generating sub-200 nm light is described. This laser uses a fundamental wavelength between about 1030 nm and 1065 nm to generate the sub-200 nm light. The final frequency conversion stage of the laser creates the sub-200 nm light by mixing a wavelength of approximately 1109 nm with a wavelength of approximately 234 nm. By proper selection of non-linear media, such mixing can be achieved by nearly non-critical phase matching. This mixing results in high conversion efficiency, good stability, and high reliability.

3 Claims, 22 Drawing Sheets

(51) Int. Cl.
 *H01S 3/23* (2006.01)
 *G02B 17/08* (2006.01)

(56) References Cited

U.S. PATENT DOCUMENTS

| | | |
|---|---|---|
| 4,467,189 A | 8/1984 | Tsuchiya |
| 4,644,221 A | 2/1987 | Gutierrez et al. |
| 4,853,595 A | 8/1989 | Alfano et al. |
| 5,120,949 A | 6/1992 | Tomasetti |
| 5,144,630 A | 9/1992 | Lin |
| 5,563,702 A | 10/1996 | Emery et al. |
| 5,572,598 A | 11/1996 | Wihl et al. |
| 5,742,626 A | 4/1998 | Mead et al. |
| 5,760,809 A | 6/1998 | Malhotra et al. |
| 5,760,899 A | 6/1998 | Eismann |
| 5,825,562 A | 10/1998 | Lai et al. |
| 5,999,310 A | 12/1999 | Shafer et al. |
| 6,064,759 A | 5/2000 | Buckley et al. |
| 6,201,257 B1 | 3/2001 | Stettner et al. |
| 6,201,601 B1 | 3/2001 | Vaez-Iravani et al. |
| 6,212,310 B1 | 4/2001 | Waarts et al. |
| 6,220,914 B1 | 4/2001 | Lee et al. |
| 6,249,371 B1 | 6/2001 | Masuda et al. |
| 6,271,916 B1 | 8/2001 | Marxer et al. |
| 6,285,018 B1 | 9/2001 | Aebi et al. |
| 6,373,869 B1 | 4/2002 | Jacob |
| 6,498,801 B1 | 12/2002 | Dudelzak et al. |
| 6,590,698 B1 | 7/2003 | Ohtsuki et al. |
| 6,608,676 B1 | 8/2003 | Zhao et al. |
| 6,816,520 B1 | 11/2004 | Tulloch et al. |
| 6,859,335 B1 | 2/2005 | Lai et al. |
| 6,888,855 B1 | 5/2005 | Kopf |
| 7,098,992 B2 | 8/2006 | Ohtsuki et al. |
| 7,136,402 B1 | 11/2006 | Ohtsuki |
| 7,313,155 B1 | 12/2007 | Mu |
| 7,339,961 B2 | 3/2008 | Tokuhisa et al. |
| 7,352,457 B2 | 4/2008 | Kvamme et al. |
| 7,463,657 B2 | 12/2008 | Spinelli et al. |
| 7,471,705 B2 | 12/2008 | Gerstenberger et al. |
| 7,525,649 B1 | 4/2009 | Leong et al. |
| 7,528,943 B2 | 5/2009 | Brown et al. |
| 7,586,108 B2 | 9/2009 | Nihtianov et al. |
| 7,593,437 B2 | 9/2009 | Staroudoumov et al. |
| 7,593,440 B2 | 9/2009 | Spinelli et al. |
| 7,609,309 B2 | 10/2009 | Brown et al. |
| 7,623,557 B2 | 11/2009 | Tokuhisa et al. |
| 7,627,007 B1 | 12/2009 | Armstrong et al. |
| 7,643,529 B2 | 1/2010 | Brown et al. |
| 7,715,459 B2 | 5/2010 | Brown et al. |
| 7,813,406 B1 | 10/2010 | Nguyen et al. |
| 7,822,092 B2 | 10/2010 | Ershov et al. |
| 7,875,948 B2 | 1/2011 | Hynecek et al. |
| 7,920,616 B2 | 4/2011 | Brown et al. |
| 7,952,633 B2 | 5/2011 | Brown et al. |
| 7,999,342 B2 | 8/2011 | Hsu et al. |
| 8,208,505 B2 | 6/2012 | Dantus et al. |
| 8,238,647 B2 | 8/2012 | Ben-Yishay et al. |
| 8,298,335 B2 | 10/2012 | Armstrong |
| 8,309,443 B2 | 11/2012 | Tanaka et al. |
| 8,319,960 B2 | 11/2012 | Aiko et al. |
| 8,391,660 B2 | 3/2013 | Islam |
| 8,503,068 B2 † | 8/2013 | Sakuma |
| 8,514,587 B2 | 8/2013 | Zhang et al. |
| 8,629,384 B1 | 1/2014 | Biellak et al. |
| 8,686,331 B2 | 4/2014 | Armstrong |
| 8,755,417 B1 | 6/2014 | Dribinski |
| 8,873,596 B2 | 10/2014 | Dribinski |
| 8,891,079 B2 | 11/2014 | Zhao et al. |
| 8,929,406 B2 | 1/2015 | Chuang et al. |
| 2001/0000977 A1 | 5/2001 | Vaez-Iravani et al. |
| 2002/0109110 A1 | 8/2002 | Some et al. |
| 2002/0114553 A1 | 8/2002 | Mead et al. |
| 2002/0191834 A1 | 12/2002 | Fishbaine |
| 2003/0043876 A1 | 3/2003 | Lublin et al. |
| 2003/0147128 A1 | 8/2003 | Shafer et al. |
| 2003/0161374 A1 | 8/2003 | Lokai |
| 2004/0080741 A1 | 4/2004 | Marxer et al. |
| 2005/0041702 A1 | 2/2005 | Fermann et al. |
| 2005/0110988 A1 | 5/2005 | Nishiyama et al. |
| 2005/0111081 A1 | 5/2005 | Shafer et al. |
| 2005/0122021 A1 | 6/2005 | Smith et al. |
| 2005/0128473 A1 | 6/2005 | Karpol et al. |
| 2005/0157382 A1 | 7/2005 | Kafka et al. |
| 2005/0190452 A1 | 9/2005 | Govorkov et al. |
| 2005/0254049 A1 | 11/2005 | Zhao |
| 2005/0254065 A1 † | 11/2005 | Stokowski |
| 2006/0038984 A9 | 2/2006 | Vaez-Iravani et al. |
| 2006/0171656 A1 | 8/2006 | Adachi et al. |
| 2006/0239535 A1 † | 10/2006 | Takada |
| 2006/0291862 A1 | 12/2006 | Kawai |
| 2007/0002465 A1 † | 1/2007 | Chuang |
| 2007/0047600 A1 | 3/2007 | Luo et al. |
| 2007/0096648 A1 | 5/2007 | Nakajima et al. |
| 2007/0103769 A1 | 5/2007 | Kuwabara |
| 2007/0146693 A1 | 6/2007 | Brown et al. |
| 2007/0188744 A1 | 8/2007 | Leslie et al. |
| 2007/0211773 A1 | 9/2007 | Gerstenberger et al. |
| 2007/0263680 A1 | 11/2007 | Staroudoumov et al. |
| 2007/0291810 A1 | 12/2007 | Luo et al. |
| 2008/0182092 A1 | 7/2008 | Bondokov et al. |
| 2008/0186476 A1 † | 8/2008 | Kusunose |
| 2008/0204737 A1 † | 8/2008 | Ogawa |
| 2009/0084989 A1 | 4/2009 | Imai |
| 2009/0108207 A1 | 4/2009 | Liu |
| 2009/0128912 A1 | 5/2009 | Okada |
| 2009/0180176 A1 | 7/2009 | Armstrong et al. |
| 2009/0185583 A1 † | 7/2009 | Kuksenkov |
| 2009/0185588 A1 | 7/2009 | Munroe |
| 2009/0296755 A1 | 12/2009 | Brown et al. |
| 2010/0103409 A1 | 4/2010 | Ohshima et al. |
| 2010/0188655 A1 | 7/2010 | Brown et al. |
| 2010/0301437 A1 | 12/2010 | Brown et al. |
| 2011/0062127 A1 | 3/2011 | Gu et al. |
| 2011/0073982 A1 | 3/2011 | Armstrong et al. |
| 2011/0085149 A1 | 4/2011 | Nathan |
| 2011/0101219 A1 | 5/2011 | Uchiyama et al. |
| 2011/0134944 A1 | 6/2011 | Kaneda et al. |
| 2011/0222565 A1 | 9/2011 | Horain et al. |
| 2011/0228263 A1 | 9/2011 | Chuang et al. |
| 2011/0279819 A1 | 11/2011 | Chuang et al. |
| 2012/0026578 A1 | 2/2012 | Sakuma |
| 2012/0033291 A1 | 2/2012 | Kneip |
| 2012/0092657 A1 † | 4/2012 | Shibata |
| 2012/0113995 A1 | 5/2012 | Armstrong |
| 2012/0120481 A1 | 5/2012 | Armstrong |
| 2012/0137909 A1 | 6/2012 | Hawes et al. |
| 2012/0160993 A1 | 6/2012 | Nevet et al. |
| 2012/0314286 A1 | 12/2012 | Chuang et al. |
| 2013/0009069 A1 | 1/2013 | Okada |
| 2013/0016346 A1 | 1/2013 | Romanovsky et al. |
| 2013/0020491 A1 | 1/2013 | Mazzillo |
| 2013/0021602 A1 | 1/2013 | Dribinski et al. |
| 2013/0064259 A1 | 3/2013 | Wakabayashi et al. |
| 2013/0077086 A1 | 3/2013 | Chuang et al. |
| 2013/0082241 A1 | 4/2013 | Kub et al. |
| 2013/0088706 A1 | 4/2013 | Chuang et al. |
| 2013/0126705 A1 | 5/2013 | Maleev |
| 2013/0169957 A1 | 7/2013 | Wolf et al. |
| 2013/0176552 A1 | 7/2013 | Brown et al. |
| 2013/0194445 A1 | 8/2013 | Brown et al. |
| 2013/0264481 A1 | 10/2013 | Chern et al. |
| 2013/0313440 A1 | 11/2013 | Chuang et al. |
| 2013/0336574 A1 | 12/2013 | Nasser-Ghodsi Mehran et al. |
| 2014/0016655 A1 | 1/2014 | Armstrong |
| 2014/0034816 A1 | 2/2014 | Chuang et al. |
| 2014/0050234 A1 | 2/2014 | Ter-Mikirtychev |
| 2014/0071520 A1 | 3/2014 | Armstrong |
| 2014/0111799 A1 | 4/2014 | Lei et al. |
| 2014/0153596 A1 | 6/2014 | Chuang et al. |
| 2014/0158864 A1 | 6/2014 | Brown et al. |
| 2014/0204963 A1 | 7/2014 | Chuang et al. |
| 2014/0291493 A1 | 10/2014 | Chuang et al. |
| 2014/0305367 A1 | 10/2014 | Chuang et al. |
| 2015/0007765 A1 | 1/2015 | Dribinski |

(56) References Cited

U.S. PATENT DOCUMENTS

| | | |
|---|---|---|
| 2015/0177159 A1 | 6/2015 | Brown et al. |
| 2015/0200216 A1 | 7/2015 | Muramatsu et al. |
| 2015/0275393 A1 | 10/2015 | Bondokov et al. |
| 2015/0294998 A1 | 10/2015 | Nihtianov |

FOREIGN PATENT DOCUMENTS

| | | |
|---|---|---|
| EP | 0532927 | 3/1993 |
| EP | 0746871 B1 | 5/2000 |
| EP | 0602983 B1 | 6/2000 |
| EP | 1194804 B1 | 7/2003 |
| EP | 1939917 A2 | 7/2008 |
| EP | 2013951 | 1/2009 |
| JP | H0511287 A | 1/1993 |
| JP | 2002-258339 A | 9/2002 |
| JP | 2003043533 A | 2/2003 |
| JP | 2006-60162 A | 3/2006 |
| JP | 200786108 | 4/2007 |
| JP | 2007-206452 A | 8/2007 |
| JP | 2007249092 A | 9/2007 |
| JP | 2007298932 A | 11/2007 |
| JP | 2009-145791 | 7/2009 |
| JP | 2010003755 | 1/2010 |
| JP | 2010-54547 | 3/2010 |
| JP | 2010-256784 | 11/2010 |
| JP | 2011-23532 A | 2/2011 |
| JP | 2011-128330 A | 6/2011 |
| WO | 9532518 A1 | 11/1995 |
| WO | 9617372 A1 | 6/1996 |
| WO | 03/069263 | 8/2003 |
| WO | 2005/022705 A2 | 3/2005 |
| WO | 2009/082460 | 7/2009 |
| WO | 2010/037106 | 4/2010 |
| WO | 2012/154468 | 11/2012 |
| WO | 2013/015940 A2 | 1/2013 |
| WO | 2013006867 A1 | 1/2013 |
| WO | 2014067754 A2 | 5/2014 |

OTHER PUBLICATIONS

Dianov et al. "Bi-doped fiber lasers: new type of high-power radiation sources", Conference on Lasers and Electro-Optics, May 6-11, 2007, 2 pages.

Kalita et al. "Multi-watts narrow-linewidth all fiber Yb-doped laser operating at 1179 nm", Optics Express, 18 (6), pp. 5920-5925 (2010).

Kashiwagi et al. "Over 10W output linearly-polarized single-stage fiber laser oscillating above 1160 nm using Yb-doped polarization-maintaining solid photonic bandgap fiber", IEEE Journal of Quantum Electronics, 47 (8), pp. 1136-1141 (2011).

Mead et al. "Solid-state lasers for 193-nm photolithogaphy", Proc. SPIE 3051, Optical Microlithogaphy X, pp. 882-889 (Jul. 7, 1997).

Saikawa et al. "52 mJ narrow-bandwidth degenerated optical parametric system with a large-aperture periodically poled MgO:LiNbO3 device", Optics Letters, 31 (#21), 3149-3151 (2006).

Sakuma et al. "High power, narrowband, DUV laser source by frequency mixing in CLBO", Advanced High-Power Lasers and Applications. Nov. 2000, pp. 7-14, Ushio Inc.

Sakuma et al. "True CW 193.4-nm light generation based on fequency conversion of fiber amplifiers", Optcs Express 19 (#16), 15020-15025 (2011).

Sasaki et al. "Progress in the growth of a CsLiB6O10 crystal and its application to ultraviolet light generation", Optical Materials, vol. 23, 343-351 (2003).

Shirakawa et al. "High-power Yb-doped photonic bandgap fiber amplifier at 1150-1200nm", Optics Express 17 (2), 447-454 (2009).

Ter-Mikirtychev et al. "Tunable LiF:F2—color center laser with an intracavity integrated-optic output coupler", Journal of Lightwave Technology, 14 (10), 2353-2355 (1996).

Yoo et al. "Excited state absorption measurement in bismuth-doped silicate fibers for use in 1160 nm fiber laser", 3rd EPS-QEOD Europhoton Conference, Paris, France, Aug. 31-Sep. 5, 2008, 1 page.

Zavartsev et al. "High efficient diode pumped mixed vanadate crystal Nd:Gd0.7Y0.3VO4 laser", International Conference on Lasers, Applications, and Technologies 2007: Advanced Lasers and Systems, Valentin A. Orlovich et al. ed., Proc. of SPIE vol. 6731, 67311P (2007), 5 pages.

File history for U.S. Appl. No. 11/735,967, filed Apr. 16, 2007 by Vladimir L. Dribinski et al.

Fu, Xiaoqian, "Higher Quantum Efficiency by Optimizing GaN Photocathode Structure", 978-1-4244-6644-3/10/ © 2010 IEEE, pp. 234-235.

International Search Report and Written Opinion dated May 13, 2014 for PCT/US2014/012902, filed Jan. 24, 2014 in the name of KLA-Tencor Corporation.

International Search Report and Written Opinion dated Jul. 11, 2014 for PCT/US2014/030989, filed Mar. 18, 2014 in the name of KLA-Tencor Corporation.

International Search Report and Written Opinion dated May 20, 2014 for PCT/US2014/016198, filed Feb. 13, 2014 in the name of KLA-Tencor Corporation.

KLA-Tencor Corporation, U.S. Appl. No. 14/248,045, filed Apr. 8, 2014 and entitled "Passivation of Nonlinear Optical Crystals".

KLA-Tencor Corporation, U.S. Appl. No. 62/059,368, filed Oct. 3, 2014 and entitled "183nm Laser and Inspection System".

KLA-Tencor Corpoation, U.S. Appl. No. 14/210,355, filed Mar. 13, 2014 and entitled "193nm Laser and an Inspection System Using a 193nm Laser".

Raoult, F. et al., "Efficient generation of narrow-bandwidth picosecond pulses by frequency doubling of femtosecond chirped pulses", Jul. 15, 1998 / ol. 23, No. 14 / Optics Letters, pp. 1117-1119.

Huang, Qiyu et al., "Back-Side Illuminated Photogate CMOS Active Pixel Sensor Structure With Improved Short Wavelength Response", IEEE Sensors Journal, vol. 11, No. 9, Sep. 2011, 5 pages.

Itzler, Mark et al., "InP-based Geiger-mode avalanche photodiode arrays for three-dimensional imaging at 1.06 μm", Proceedings of SPIE, vol. 7320 (2000), 12 pages.

Niclass, Cristiano et al., "Design and Characterization of a CMOS 3-D Image Sensor Based on Single Photon Avalanche Diodes", IEEE Journal of Solid-State Circuits, vol. 40, No. 9, Sep. 2005, 8 pages.

Paetzel, Rainer et al., "Activation of Silicon Wafer by Excimer Laser" 18th IEEE Conf. Advanced Thermal processing of Semiconductors—RTP 2010, 5 pages.

Stevanovic, Nenad et al., "A CMOS Image Sensor for High-Speed Imaging", 2000 IEEE Int'l. Conference Solid-State Circuits, 3 pages.

Dulinski, Wojciech et al., "Tests of a backside illuminated monolithic CMOS pixel sensor in an HPD set-up", Nuclear Instruments and Methods in Physics Research A 546 (2005) 274-280, 7 pages.

Sarubbi, F et al, "Pure boron-doped photodiodes: a solution for radiation detection in EUV lithography", Proceedings of the 38th EP Solid-State Device Research Conf., Edinburgh Int'l. Conf. Centre, Endiburgh, Scotland, UK, Sep. 15-19, 2008, Piscataway, NJ: IEEE, US, pp. 278-281.

Sakic, Agata, "Boron-layer silicon photodiodes for high-efficiency low-energy electron detection", Solid-State Electronics 65-66 (2011), pp. 38-44.

Omatsu, Takashige et al., "High repetition rate Q-switching performance in transversely diode-pumped Nd doped mixed gadolinium yttrium vanadate bounce laser", Optics Express vol. 14, Issue 7, pp. 2727-2734, Apr. 3, 2006.

Utsumi, Vacuum Microelectrnoics: What's New and Exciting, IEEE vol. 38, No. 10, Oct. 1991, 8 pgs.

Armstrong, Carter M., The Quest for the Ultimate Vacuum Tube, Spectrum IEEE, Dec. 2015, 4 pgs.

Serbun, Pavel et al., Stable field emission of single B-doped . . . , JVSTB, 31, 02B101 (2013); doi: 10.1116/1.4765088, 7 pgs.

Sato, T. et al., Fabrication and characterization of HfC coated . . . , J. Vac. Sci. Technol. B 2194), published Jul. 31, 2003, 5 pgs.

Nagao, Masayoshi, Fabrication of a Field Emitter Array with a Built-In Einzel Lens, JJAP 48 (2008) 06FK02, 4 pgs.

(56) References Cited

OTHER PUBLICATIONS

Rakhshandehroo, M.R., et al., Fabrication of a self-aligned silicon field emission . . . , JVSTB, 16, 765 (1998); doi: 10.1116/1,589900, 6 pgs.

Rakhshandehroo, M.R., et al., Field emission from gated Si emitter tips with precise . . . , JVSTB, 15, 2777 (1997); doi: 10.1116/1.589726, 6 pgs.

Ding, Meng, Field Emission from Silicon, MIT 2001, 277 pgs.

Koike, Akifuni, Field Emitter Equipped With a Suppressor to Control Emission Angel, IEEE Electron Device Letters, vol. 34, No. 5, May 2013, 3 pgs.

Nagao, Masayoshi, Cathode Technologies for Field Emission Displays, IEJ Trans 2006; 1:171-178, 8 pgs.

Neo, Yoichiro, Electron Optical Properties of Microcolumn with Field Emitter, JJAP 52 (2013) 036603, 5 pgs.

Fowler, R.H. et al., Electron Emission in Intense Electric Fields, Mar. 31, 1928, 9 pgs.

Fanton, J. T., et al., "Multiparameter Measurements of Thin Films Using beam-profile reflectometry", Journal of Applied Physics, vol. 73, No. 11, p. 7035 (1993).

Grubisic, D., et al., "New Silicon Reach-Through Avalanche Photodiodes with Enhanced Sensitivity in the DUV/UV Wavelength Range", MIPRO 2013, May 20-24, 2013, Opatija, Croatia, pp. 48-54.

Sakuma, et al., True CW 193.4-nm light generation based on frequency conversion of fiber amplifiers, p. 15020-15025, Jul. 20, 2011.†

† cited by third party

193NM LASER AND INSPECTION SYSTEM

PRIORITY APPLICATION

The present application claims priority to U.S. Provisional Patent Application 61/764,441, filed on Feb. 13, 2013 and incorporated by reference herein.

RELATED APPLICATIONS

The present application is related to U.S. patent application Ser. No. 13/797,939 entitled "Solid-state 193 nm laser and an Inspection System using a Solid-State 193 nm laser", by Chuang et al. and filed May 12, 2013, which is incorporated by reference herein. This application is also related to U.S. patent application Ser. No. 11/735,967, entitled "Coherent light generation below about 200 nm", by Dribinski et al. and filed Apr. 16, 2007, PCT Published Application WO2012/154468 by Lei et al. and published Nov. 15, 2012, U.S. Provisional Application 61/538,353, entitled "Solid-State 193 nm Laser And An Inspection System Using A Solid-State 193 nm Laser", by Chuang et al. and filed Sep. 23, 2011, U.S. Provisional Application 61/559,292 entitled "Solid-State 193 nm Laser And An Inspection System Using A Solid-State 193 nm Laser", by Chuang et al. and filed Nov. 14, 2011, U.S. Provisional Application 61/591,384, entitled "Solid-State 193 nm Laser And An Inspection System Using A Solid-State 193 nm Laser", by Chuang et al. and filed Jan. 27, 2012, U.S. Provisional Application 61/603,911, entitled "Solid-State 193 nm Laser And An Inspection System Using A Solid-State 193 nm Laser", Chuang et al. and filed Feb. 27, 2012, U.S. patent application Ser. No. 13/558,318, entitled "193 nm Laser and Inspection System using 193 nm Laser", by Chuang et al. and filed Jul. 25, 2012, U.S. Provisional Application 61/666,675 entitled "Scan rate for Continuous Motion of a Crystal in a Frequency Converted Laser", by Armstrong and filed Jun. 29, 2012, U.S. patent application Ser. No. 14/022,190 entitled "Solid State Illumination Source And Inspection System", by Armstrong and filed Sep. 9, 2013, and U.S. patent application Ser. No. 14/158,615 entitled "193 nm Laser and Inspection System" by Chuang et al. and filed on Jan. 17, 2014. All of the above applications are incorporated by reference herein.

BACKGROUND OF THE DISCLOSURE

Field of the Disclosure

The present application relates to a solid-state laser that generates light near 193 nm and is suitable for use in photomask, reticle, or wafer inspection.

Related Art

The integrated circuit industry requires inspection tools with increasingly higher resolution to resolve ever smaller features of integrated circuits, photomasks, solar cells, charge coupled devices etc., as well as detect defects whose sizes are of the order of, or smaller than, feature sizes. Short wavelength light sources, e.g. sources generating light under 200 nm, can provide such resolution. Specifically for photomask or reticle inspection, it is desirable to inspect using a wavelength identical, or close, to the wavelength that will be used for lithography, e.g. substantially 193.368 nm, as the phase-shifts of the inspection light caused by the patterns will be identical or very similar to those caused by the same patterns during lithography. However, the light sources capable of providing such short wavelength light are practically limited to excimer lasers and a small number of solid-state and fiber lasers. Unfortunately, each of these lasers has significant disadvantages.

An excimer laser generates an ultraviolet light, which is commonly used in the production of integrated circuits. An excimer laser typically uses a combination of a noble gas and a reactive gas under high pressure conditions to generate the ultraviolet light. A conventional excimer laser generating 193 nm wavelength light, which is increasingly a highly desirable wavelength in the integrated circuit industry, uses argon (as the noble gas) and fluorine (as the reactive gas). Unfortunately, fluorine is toxic and corrosive, thereby resulting in high cost of ownership. Moreover, such lasers are not well suited to inspection applications because of their low repetition rate (typically from about 100 Hz to several kHz) and very high peak power that could result in damage of samples during inspection. Furthermore, high-speed inspection typically requires minimum laser pulse repetition rates of multiple MHz (e.g. greater than 50 MHz in some cases) in order to allow high-speed image or data acquisition with low noise.

A small number of solid state and fiber based lasers producing sub-200 nm output are known in the art. Unfortunately, most of these lasers have very low power output (e.g. under 60 mW), or very complex design, such as two different fundamental sources or eighth harmonic generation, both of which are complex, unstable, expensive and/or commercially unattractive.

Therefore, a need arises for a laser capable of generating 193 nm light yet overcoming the above disadvantages.

SUMMARY OF THE DISCLOSURE

A laser for generating ultraviolet light with a vacuum wavelength near 193 nm, such as in a wavelength range between 190 nm and 200 nm, is described. This laser includes a fundamental source and multiple stages for generating harmonic, sum and other frequencies. In preferred embodiments, the fundamental source can generate a fundamental frequency corresponding to a wavelength of approximately 1064 nm to 1065 nm. In other embodiments, the fundamental can generate a wavelength of approximately 1053 nm or approximately 1047 nm. Fundamental wavelengths in the range from about 1047 nm to 1065 nm can be used in one or more embodiments of the sub-200-nm laser described herein. Lasers that can generate wavelengths in this range include Yb-doped fiber lasers, Nd:YAG lasers (neodymium-doped yttrium aluminum garnate), neodymium-doped yttrium orthovanadate lasers, and Nd:YLF (neodymium-doped yttrium lithium fluoride) lasers. Where a wavelength value without qualification is given in this specification, it is to be assumed that wavelength value refers to the wavelength in vacuum.

A first stage uses a portion of the fundamental frequency to generate a wavelength of approximately 1109 nm. In one embodiment a fiber is used to generate or amplify light at a wavelength of approximately 1109 nm from a portion of the fundamental wavelength. In a second embodiment of this stage, an OPO or OPA is used to generate or amplify a wavelength near 2218 nm from a portion of the fundamental. In this second embodiment, the wavelength near 2218 nm is frequency-doubled to create light at a wavelength of approximately 1109 nm.

In one embodiment a second stage can generate a second harmonic frequency from a portion of the fundamental frequency. Generating a second harmonic of a wavelength near 1064 nm, 1053 nm or 1047 nm is well known. Several different non-linear crystals can be used to do this, including, but not limited to, KTP (potassium titanyl phosphate), KDP (potassium dihydrogen phosphate), KBBF (potassium fluoroboratoberyllate), CBO (cesium triborate), CLBO (cesium lithium borate), BBO (beta barium borate), LBO (lithium triborate) and LB4 (lithium tetraborate). A third stage generates a wavelength of approximately 234 nm from another portion of the fundamental and second harmonic. Apparatus and methods for generating a wavelength of approximately 234 nm from the fundamental and the second harmonic are described below.

In an alternative embodiment a second stage can generate a wavelength of approximately 1171 nm from a portion of the fundamental frequency, or from a portion of the approximately 1109 nm wavelength light. A third stage generates the fifth harmonic of the approximately 1171 nm wavelength in order to create a wavelength of approximately 234 nm.

In the above described embodiments, a fourth stage combines the wavelength near 234 nm with the wavelength near 1109 nm to generate a wavelength near 193 nm. In some embodiments the wavelength generated in the fourth stage may be substantially 193.4 nm. In some preferred embodiments this frequency combination may be achieved using near non-critical phase matching in a CLBO crystal (the phase matching angle is approximately 85° at a temperature near 120° C.). This results in good conversion efficiency, low walk-off and good stability. In some embodiments, BBO may be used instead of CLBO. For type I mixing in BBO, the phase matching angle is approximately 57° at a temperature near 120° C., the walk-off is larger than for CLBO (about 98 mrad compared with about 7 mrad), but $d_{eff}$ is about 70% larger than for CLBO (about 1.9 pm $V^{-1}$ compared with about 1.1 pm $V^{-1}$). Type II mixing in BBO is also possible at a phase matching angle of about 63°, with a lower $d_{eff}$ (approximately 0.6 pm $V^{-1}$) and a walk-off angle of about 85 mrad. Since CLBO and BBO are hygroscopic materials, in one embodiment the crystal is operated at a temperature around 120° C. or higher to prevent absorption of water from the environment. In another embodiment, the crystal is kept protected from humidity, for example by enclosing the crystal in a purged low-humidity environment, and the crystal is operated at a lower temperature, such as one near 100° C., 80° C. or 50° C. When the crystal operating temperature is different from 120° C., an appropriate change must be made to the phase-matching angle. In some preferred embodiments, the non-linear crystal used in this and other frequency-conversion stages is a hydrogen-annealed crystal as described in co-pending U.S. patent application Ser. No. 13/488,635 filed on Jun. 1, 2012 by Chuang et al, and claiming priority to U.S. Provisional Application 61/544,425 filed on Oct. 7, 2011. Both of these applications are incorporated by reference herein.

In one embodiment, the third stage can combine a portion of the second harmonic frequency with a portion of the fundamental to generate a third harmonic frequency. In this embodiment, the third stage uses another portion of the second harmonic to generate or amplify a wavelength near 689 nm using an OPO or OPA. This embodiment of the third stage combines the third harmonic frequency and the wavelength near 689 nm to generate a sum frequency corresponding to a wavelength of approximately 234 nm. In some embodiments, the combination of the third harmonic and the wavelength near 689 nm is done using a CLBO crystal. At a temperature near 120° C. the phase matching angle is approximately 75°, $d_{eff}$ is about 0.9 pm $V^{-1}$, and the walk-off angle is about 20 mrad. In other embodiments, the combination of the third harmonic and the wavelength near 689 nm is done using a BBO crystal. At a temperature near 120° C., the phase matching angle is approximately 55°, $d_{eff}$ about 1.6 pm $V^{-1}$, and the walk-off angle is about 85 mrad.

In an alternative embodiment, the third stage generates a fourth harmonic frequency from the second harmonic frequency. In this embodiment, the third stage uses a portion of the fundamental to generate or amplify a wavelength near 1954 nm using an OPO or OPA. This embodiment of the third stage combines the wavelength near 1954 nm with the fourth harmonic to generate a wavelength near 234 nm. In some embodiments, the combination of the fourth harmonic and the wavelength near 1954 nm is done using an LBO crystal, an LB4 crystal, a CLBO crystal or a BBO crystal.

In another embodiment, the third stage generates a fifth harmonic frequency from a wavelength of approximately 1171 nm. The fifth harmonic of a wavelength of near 1171 nm has a wavelength near 234 nm. In some embodiments, the approximately 234 nm wavelength has a wavelength of substantially 234.2 nm. The fifth harmonic of the wavelength near 1171 nm is created by first creating a second harmonic from a portion of the light at a wavelength near 1171 nm. This may be done, for example, using LBO, which is phase matched at an angle of about 83° for a temperature near 120° C., has a $d_{eff}$ of about 0.8 pm $V^{-1}$, and has a low walk-off of about 6 mrad. In one embodiment, the second harmonic is converted to a fourth harmonic, and the fourth harmonic is combined with a portion of the light at 1171 nm to create a fifth harmonic. In another embodiment, a portion of the second harmonic harmonic is combined with a portion of the light at a wavelength near 1171 nm to create a third harmonic, then the third harmonic is combined with a portion of the second harmonic to create a fifth harmonic. Non-linear crystals such as CLBO and BBO are suitable for creating the third, fourth and fifth harmonics of a wavelength 1171 nm. Other non-linear materials such as LB4 may be suitable for some of the conversion steps.

In some embodiments, the second stage generates a wavelength of approximately 1171 nm from a portion of the fundamental. In one embodiment, a portion of the light at the wavelength near 1109 nm is shifted to a wavelength near 1171 nm by first-order Raman shift. The first-order Raman shift gain has a broad peak near 440 $cm^{-1}$, so the second-order Raman shift is very effective at shifting a wavelength near 1109 nm to a wavelength near 1171 nm. In another embodiment, the wavelength of approximately 1171 nm is generated by second-order Raman scattering of a portion of the fundamental wavelength. The second-order Raman shift gain has a broad peak near 880 $cm^{-1}$, so the second-order Raman shift can be effective at shifting a fundamental near 1064 nm or near 1053 nm to a wavelength near 1171 nm.

In another embodiment, the laser can also include an optical amplifier for amplifying the fundamental frequency.

A method of generating light with a wavelength between about 190 nm and 200 nm, such as a wavelength of approximately 193 nm, is also described. This method includes generating a fundamental frequency of approximately 1064 nm, approximately 1053 nm or approximately 1047 nm. A portion of the fundamental frequency can be used to generate a wavelength of approximately 1109 nm. Another portion of the fundamental frequency can be used to generate a second harmonic frequency. Another portion of the fundamental frequency can be combined with the second harmonic frequency to generate a wavelength of approximately 234 nm. The approximately 1109 nm wavelength and the approximately 234 nm can be combined to generate a wavelength of approximately 193.4 nm.

An alternative method of generating approximately 193 nm wavelength light is also described. This method includes generating a fundamental frequency of approximately 1064 nm, approximately 1053 nm or approximately 1047 nm. A portion of the fundamental frequency can be used to generate a wavelength of approximately 1109 nm. Another portion of the fundamental frequency can be used to generate a wavelength of approximately 1171 nm. The wavelength of approximately 1171 nm can be converted to its fifth harmonic at a wavelength of approximately 234 nm. The approximately 1109 nm wavelength and the approximately 234 nm can be combined to generate a wavelength of approximately 193.4 nm.

A pulse multiplier is also described. This pulse multiplier includes a laser system for generating a regular series of input laser pulses. The laser system can include a light source at approximately 1064 nm, 1053 nm or 1047 nm and frequency conversion stages generating the input laser pulses at approximately 193 nm. A beam splitter can receive the input laser pulses. A set of mirrors can create a ring cavity including the beam splitter, wherein the beam splitter directs a part of, or substantially all of, each input pulse into the ring cavity, and wherein the beam splitter further directs a fraction of each pulse out of the ring each time that pulse traverses the ring.

An inspection system incorporating a 193 nm laser and a coherence reducing subsystem comprising a dispersive element and/or an electro-optic modulator is also described.

An optical inspection system for inspecting a surface of a photomask, reticle, or semiconductor wafer for defects is also described. This system can include a laser system for generating a beam of radiation at a wavelength between about 190 nm and 200 nm. This laser system can include a generator for generating a wavelength near 1109 nm that is used to create the sub-200-nm beam of radiation. The laser system may further include an annealed crystal and a housing to maintain the annealed condition of the crystal. The light reflected or scattered from the article being inspected is used to determine the presence of defects. In some embodiments, both transmitted and reflected light are collected and are used together for determining the presence of defects. In some embodiments, the transmitted and reflected light are collected on the same detector to ensure proper registration between the two sets of data.

An inspection system for inspecting a surface of a sample is also described. This inspection system includes an illumination subsystem configured to produce a plurality of channels of light, each channel of light produced having differing characteristics from at least one other channel of light energy. The illumination subsystem includes a laser for generating 193 nm wavelength light for at least one channel. Optics are configured to receive the plurality of channels of light and combine the plurality of channels of light energy into a spatially separated combined light beam and direct the spatially separated combined light beam toward the sample. A data acquisition subsystem includes at least one detector configured to detect reflected light from the sample. The data acquisition subsystem can be configured to separate the reflected light into a plurality of received channels corresponding to the plurality of channels of light.

A catadioptric imaging system with dark-field illumination is also described. This system can include an ultraviolet (UV) light source for generating UV light. This UV light source can include a laser system for generating a beam of radiation at a wavelength between about 190 nm and 200 nm. This laser system can include a generator for generating a wavelength near 1109 nm that is used to create the sub-200-nm beam of radiation. The laser system may further include an annealed crystal and a housing to maintain the annealed condition of the crystal. Adaptation optics are also provided to control the illumination beam size and profile on the surface being inspected. The catadioptric imaging system also includes a catadioptric objective, a focusing lens group, and a zooming tube lens section in operative relation to each other. A prism can be provided for directing the UV light along the optical axis at normal incidence to a surface of a sample and directing specular reflections from surface features of the sample as well as reflections from optical surfaces of the objective along an optical path to an imaging plane.

A surface inspection apparatus is also described. This apparatus can include a laser system for generating a beam of radiation at a wavelength between about 190 nm and 200 nm. This laser system can include a generator for generating a wavelength near 1109 nm that is used to create the sub-200-nm beam of radiation. The laser system may further include an annealed crystal and a housing to maintain the annealed condition of the crystal. An illumination system can be configured to focus the beam of radiation at a non-normal incidence angle relative to a surface to form an illumination line on the surface substantially in a plane of incidence of the focused beam. The plane of incidence is defined by the focused beam and a direction that is through the focused beam and normal to the surface.

A collection system can be configured to image the illumination line. In one embodiment, the collection system can include an imaging lens for collecting light scattered from a region of the surface comprising the illumination line. A focusing lens can be provided for focusing the collected light. A device including an array of light sensitive elements can also be provided. In this array, each light sensitive element of the array of light sensitive elements can be configured to detect a corresponding portion of a magnified image of the illumination line.

An optical system for detecting anomalies of a sample is also described. This optical system includes a laser system for generating sub-200-nm wavelength light. The laser system includes a light source, an annealed, frequency-conversion crystal, a housing, and beam shaping optics. The housing is provided to maintain an annealed condition of the crystal. The beam shaping optics can be configured to receive a beam from the light source and focus the beam to an elliptical cross section at a beam waist in or proximate to the crystal.

First optics can direct a first beam of radiation along a first path onto a first spot on a surface of the sample. In some embodiments, second optics can direct a second beam of radiation along a second path onto a second spot on a surface of the sample. The first and second paths are at different angles of incidence to the surface of the sample. Collection optics can include a curved mirrored surface that receives scattered radiation from the first or the second spot on the sample surface and originating from the first or second beam. The collection optics focuses the scattered radiation to a first detector. The first detector provides a single output value in response to the radiation focused onto it by said curved mirrored surface. An instrument can be provided that causes relative motion between the sample and the first and second beams so that the spots are scanned across the surface of the sample.

DETAILED DESCRIPTION OF THE DRAWINGS

Figure 1A:
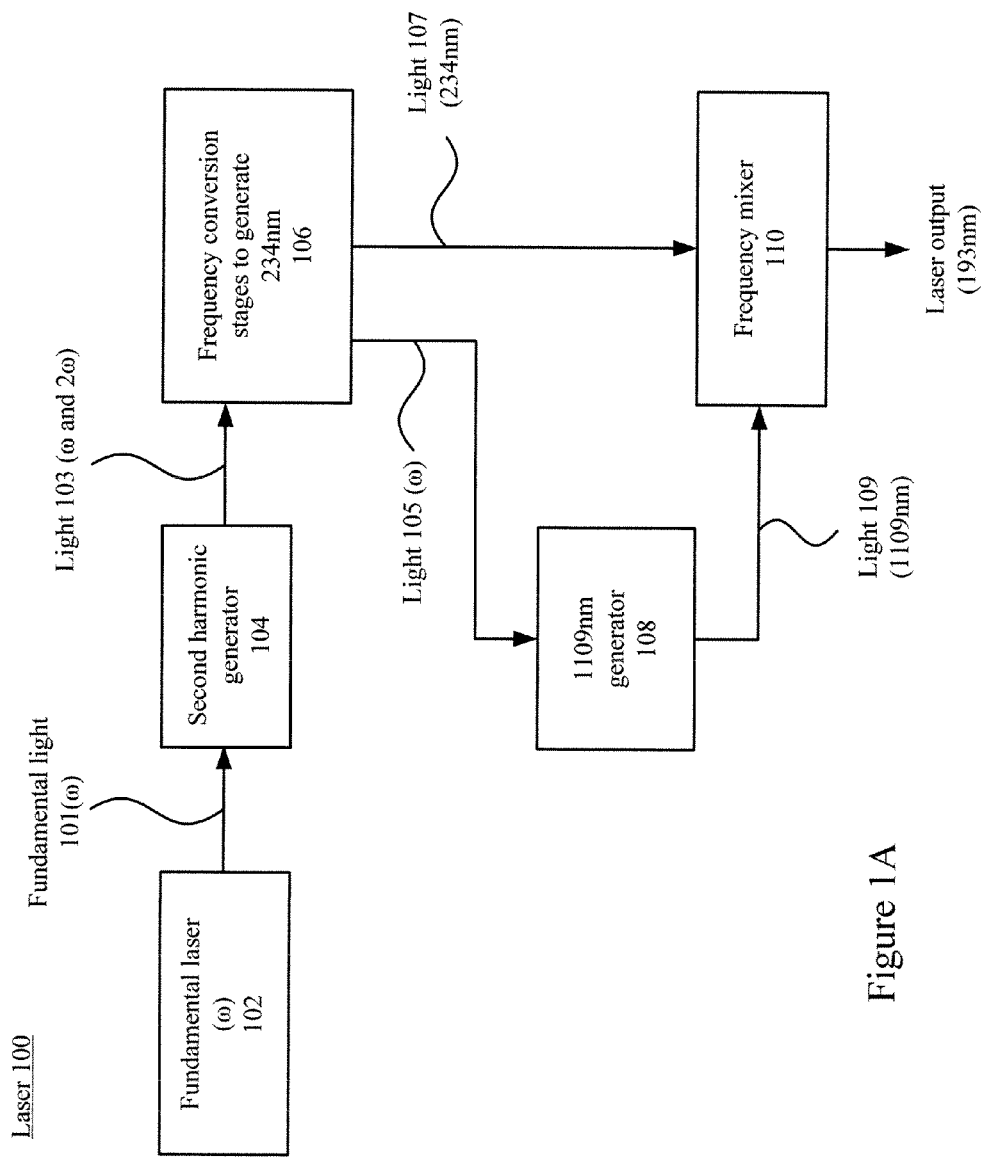
FIG. 1A illustrates a block diagram of an exemplary laser for generating 193 nm light using a fundamental wavelength near 1064 nm, 1053 nm, or 1047 nm.

An improved laser for generating light with a wavelength near 193 nm, such as a wavelength in the range from 190 nm to 200 nm, is described. FIG. 1A illustrates a simplified block diagram of an exemplary embodiment of a laser 100 for generating 193 nm light. This laser 100 generates the output wavelength near 193 nm by mixing a wavelength of approximately 1109 nm with a wavelength of approximately 234 nm. The approximately 1109 nm light and the approximately 234 nm light are generated from the same fundamental laser.

In one embodiment, laser 100 includes a fundamental laser 102 operating at a wavelength near 1064 nm, which generates a fundamental light 101 at frequency ω. In other embodiments, other wavelengths such as 1047 nm or 1053 nm can be used for the fundamental laser 102. The fundamental laser 102 may be a fiber laser, or may be based on Nd:YAG, Nd-doped yttrium orthovanadate or Nd:YLF. The fundamental laser 102 is preferably a pulsed laser, such as a mode-locked laser or a Q-switched laser.

A second harmonic generator 104 creates the second harmonic 2ω of the fundamental. The second harmonic generator 104 outputs a light 103 that includes the second harmonic 2ω and a part of the fundamental ω that is not consumed in the second harmonic generation process. The light 103 from the second harmonic generator 104 is directed to frequency conversion stages 106.

With the light 103 (i.e. from the fundamental ω and the second harmonic 2ω), the frequency conversion stages 106 generate a light 107 having a wavelength near 234 nm, such as a wavelength of substantially 234.2 nm. Frequency conversion stages 106 also output a light 105 including the unconsumed fundamental (ω). Exemplary embodiments of frequency conversion stages 106 are described below.

A 1109 nm generator 108 generates a wavelength near 1109 nm from a portion of the light 105 at the fundamental frequency ω. Although FIG. 1A shows that the light 105 is output by the frequency conversion stages 106, in other embodiments (not shown) that unconsumed fundamental could be taken directly from the fundamental laser 102 or from the output of the second harmonic generator 104. In yet other embodiments, not shown, the unconsumed fundamental from the output of the 1109 nm generator 108 is directed to the second harmonic generator 104 and/or the frequency conversion stages 106. There are many different ways to direct the fundamental between the second harmonic generator 104, the frequency generator 106, and the 1109 nm generator 108. All such different schemes are within the scope of the present invention. Exemplary embodiments of the 1109 nm generator are described below.

A frequency mixer 110 generates the laser output having a wavelength near 193 nm by mixing the light 109 having a wavelength of approximately 1109 nm with the light 107 having a wavelength of approximately 234 nm. This mixing is nearly non-critically phase matched in CLBO at a temperature near 80-120° C. Notably, this mixing results in good conversion efficiency, low walk-off and good stability. Even lower temperatures, such as about 30-80° C. result in good conversion efficiency, low walk-off and acceptable stability and may be used in some embodiments. In some embodiments, BBO may be used instead of CLBO.

Figure 1B:
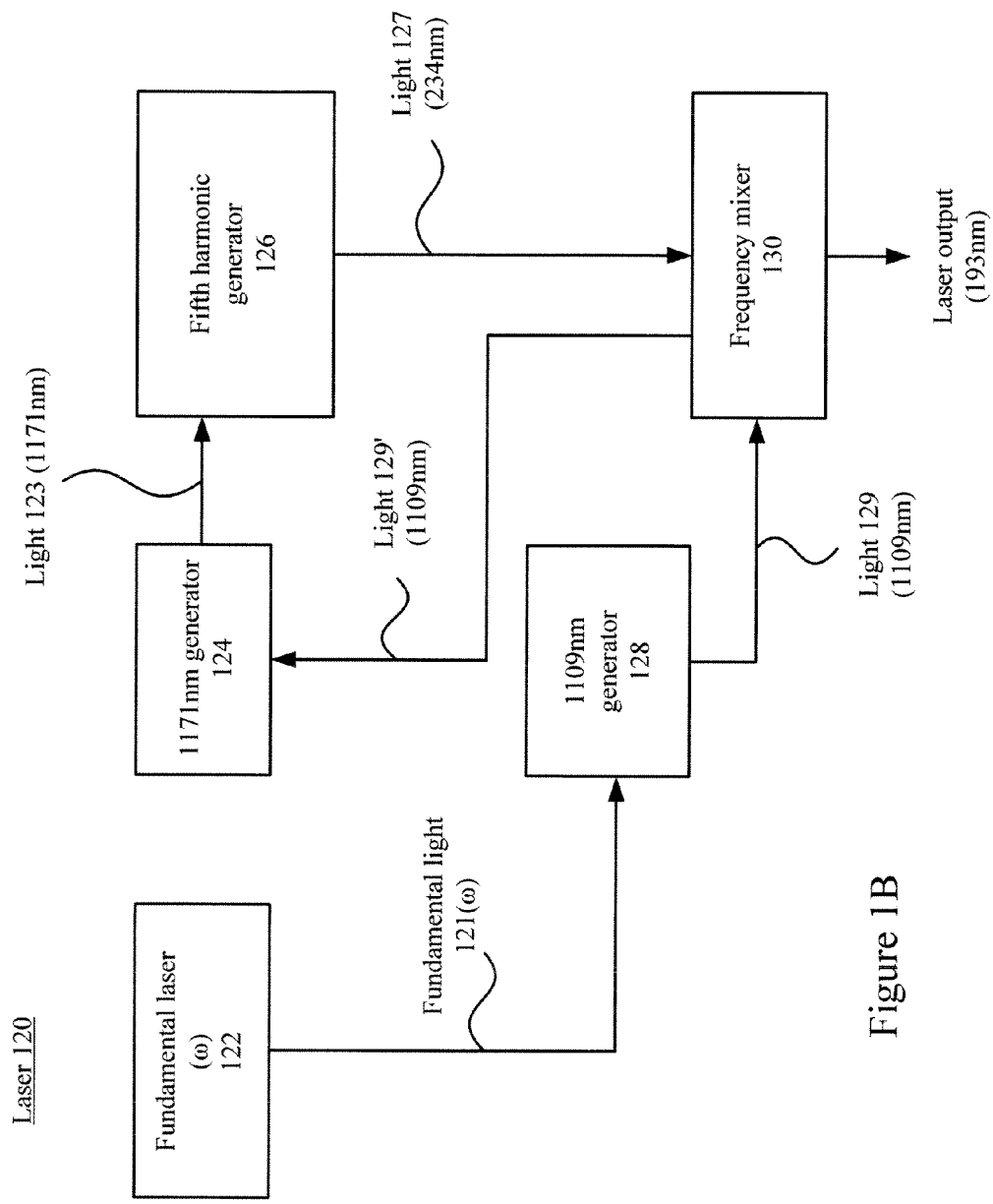
FIG. 1B illustrates a block diagram of an alternative exemplary laser for generating 193 nm light using a fundamental wavelength near 1064 nm, 1053 nm, or 1047 nm.

FIG. 1B illustrates a simplified block diagram of an alternative embodiment of a laser 120 for generating 193 nm light. In this embodiment, laser 120 includes a fundamental laser 122 operating at a wavelength near 1064 nm, which generates a fundamental light 121 at frequency ω. As described above, other wavelengths such as 1047 nm or 1053 nm can be used for the fundamental laser 122. The fundamental laser 122 may be a fiber laser, or may be based on Nd:YAG, Nd-doped orthovandate or Nd:YLF. The fundamental laser 122 is preferably a pulsed laser, such as a mode-locked laser or a Q-switched laser.

A 1109 nm generator 128 generates a light 129 having a wavelength near 1109 nm from the fundamental light 121. A frequency mixer 110 generates the laser output having a wavelength near 193 nm by mixing the light 129 having a wavelength of approximately 1109 nm with a light 127 having a wavelength of approximately 234 nm. This mixing is nearly non-critically phase matched in CLBO at a temperature near 80-120° C. Notably, this mixing results in good conversion efficiency, low walk-off and good stability. In some embodiments, BBO may be used instead of CLBO.

In this embodiment, a 1171 nm generator 124 creates a light 123 having a wavelength near 1171 nm from a portion of a light 129' at a wavelength near 1109 nm. The light 129' may be taken from unconsumed 1109 nm from frequency mixing stage 130 as shown, or may be taken directly from the 1109 nm generator 128 (not shown). The 1171 nm generator 124 outputs a light 123 at a wavelength of approximately 1171 nm, which is directed to a fifth harmonic generator 126. The fifth harmonic generator 126 generates light near 234 nm, such as a wavelength of substantially 234.2 nm, by creating the fifth harmonic of the approximately 1171 nm light. Exemplary embodiments of the 1171 nm generator 124 and the fifth-harmonic generator 126 are described below.

Figure 1C:
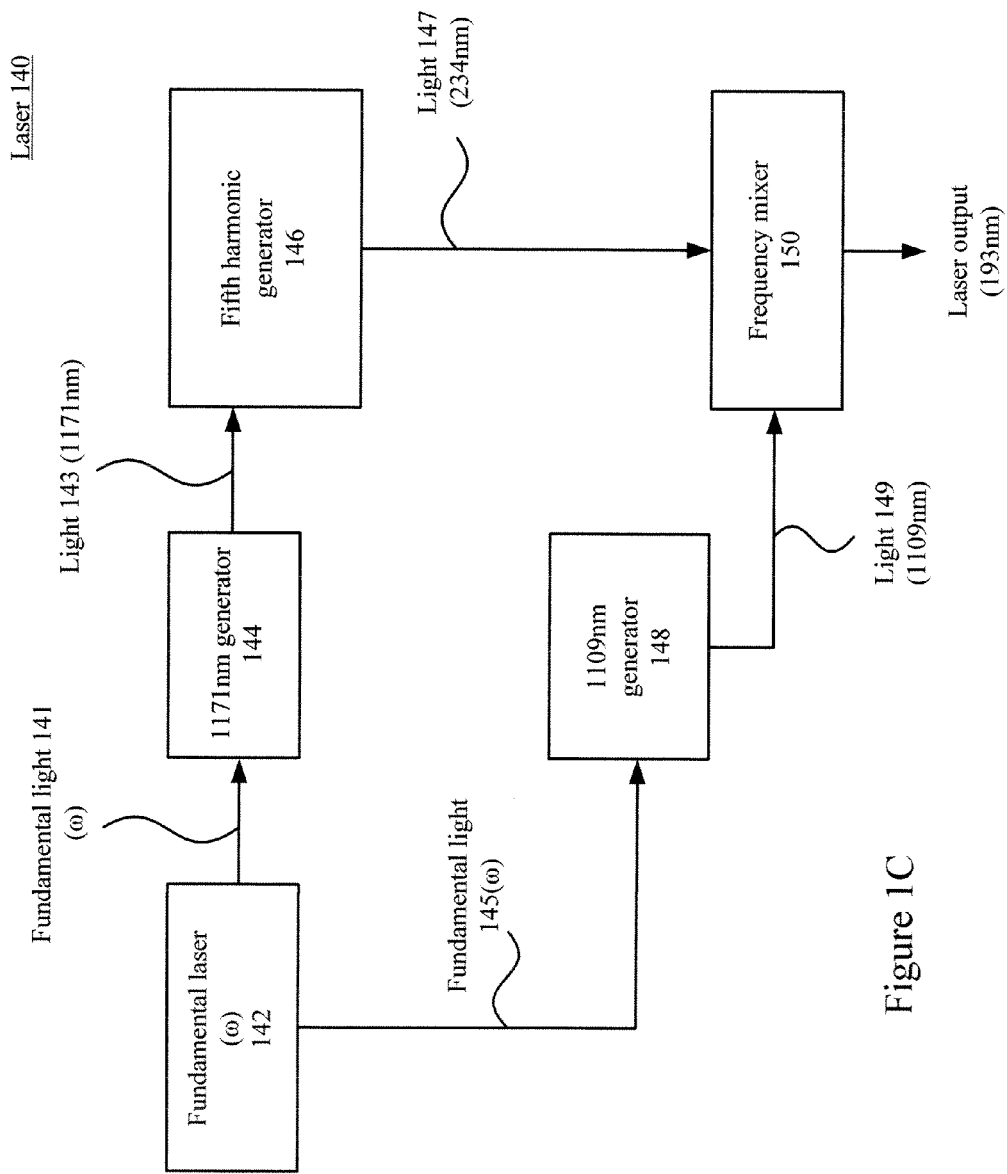
FIG. 1C illustrates a block diagram of another alternative exemplary laser for generating 193 nm light using a fundamental wavelength near 1064 nm or 1053 nm.

FIG. 1C illustrates a simplified block diagram of another alternative embodiment of a laser 140 for generating 193 nm light. In this embodiment, laser 140 includes a fundamental laser 142 operating at a wavelength near 1064 nm, which generates a fundamental light 141 at frequency ω. As described above, other wavelengths such as 1053 nm can be used for the fundamental laser, and any of the above described lasers may be used for the fundamental laser 142. The fundamental laser 142 is preferably a pulsed laser, such as a mode-locked laser or a Q-switched laser.

An 1171 nm generator 144 creates a light 143 having a wavelength near 1171 nm from a portion of the fundamental light 141. In one embodiment, this portion of the fundamental light 141 may be taken directly from the output of the fundamental laser 142. In another embodiment (not shown), an unconsumed fundamental from the 1109 nm generator 148 can be used by the 1171 nm generator 144. The 1171 nm generator 144 outputs a light 143 at a wavelength of approximately 1171 nm. The light 143 is directed to a fifth harmonic generator 146 that generates light near 234 nm, such as a wavelength of substantially 234.2 nm, by creating the fifth harmonic of the approximately 1171 nm light. The fifth harmonic generator 146 may function in a substantially similar manner to the fifth harmonic generator 126 (FIG. 1B). Exemplary embodiments of the 1171 nm generator 144 and the fifth harmonic generator 146 are described below.

The 1109 nm generator 148 generates a wavelength near 1109 nm from a portion of a fundamental light 145 provided by the fundamental laser 142. In some embodiments (not shown), the fundamental light 145 for the 1109 nm generator 148 may be taken from an unconsumed fundamental from the 1171 nm generator 144. In other embodiments (not shown), the unconsumed fundamental from the 1109 nm generator 148 may be directed to the 1171 nm generator 144. The 1109 nm generator 148 operates substantially similarly to the 1109 nm generators 108 and 128 described above. Exemplary embodiments of the 1109 nm generator 148 are described below.

Figure 2A:
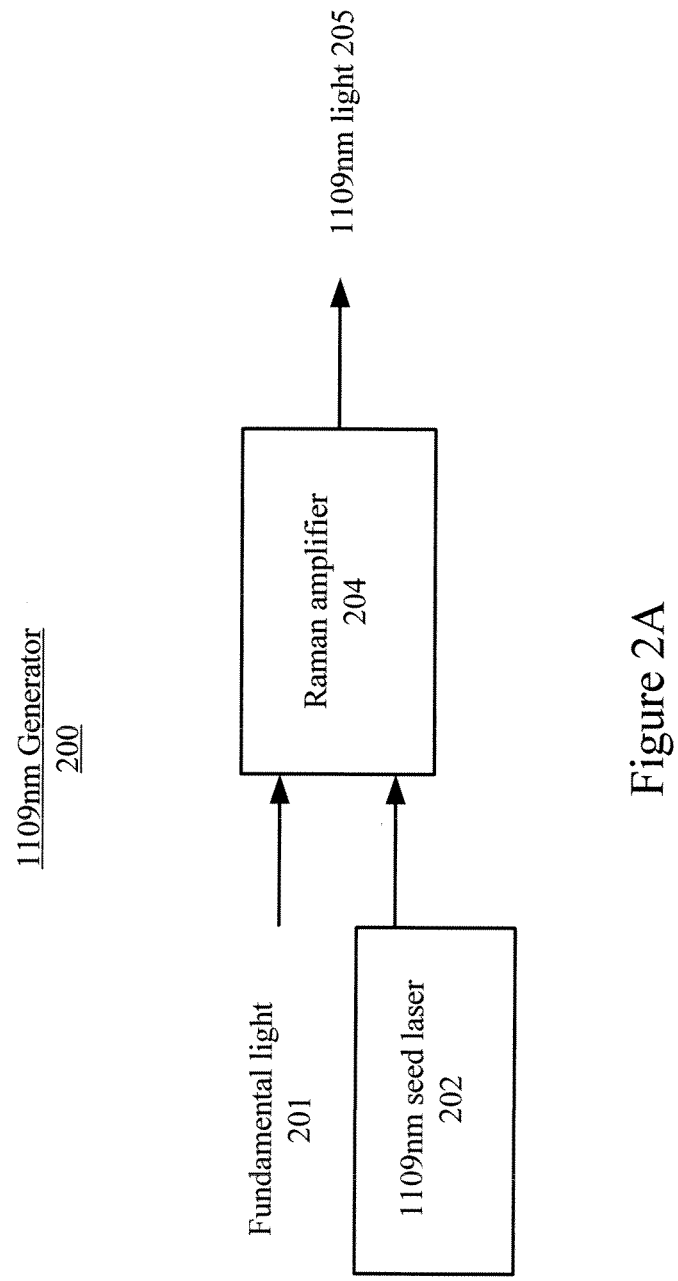
FIG. 2A illustrates a block diagram of one exemplary generator for generating a wavelength of approximately 1109 nm.

FIG. 2A illustrates a simplified block diagram of an exemplary embodiment of an 1109 nm generator 200 that can perform the functions of the 1109 nm generator 108 (FIG. 1A), the 1109 nm generator 128 (FIG. 1B), and the 1109 nm generator 148 (FIG. 1C). In this embodiment, a light 205 at a wavelength of approximately 1109 nm is generated from a fundamental light 201 using a Raman amplifier 204. The Raman amplifier 204 may include a fused-silica fiber or a germania-doped fused silica fiber. The Raman gain of a fused silica or germania-doped fused silica fiber has a broad peak centered near 440 cm$^{-1}$ of frequency shift. The useful gain extends from a shift of about 300 cm$^{-1}$ to a shift of about 500 cm$^{-1}$. Any fundamental wavelength between about 1050 nm and about 1073 nm is within 300 to 500 cm$^{-1}$ of 1109 nm, and so such wavelengths are ideally suited for use as the fundamental wavelength. Wavelengths just outside this range (such as 1047 nm) may be useable depending on the required specification of the output wavelength. A fundamental wavelength of about 1030 nm could be used with a second-order Raman shift. The advantage of a germania-doped fiber over undoped fused silica is that the Raman gain is higher, so a shorter length of fiber can suffice. The advantage of undoped fused silica fiber is that it is less expensive and it is not hygroscopic.

The Raman amplifier 204 amplifies the light from an 1109 nm seed laser 202. The seed laser 202 is a stable, narrow-band laser that generates a light at the desired wavelength close to 1109 nm. In some preferred embodiments, the output of the seed laser 202 may be between 1 mW and 250 mW. In preferred embodiments, the seed laser 202 may be a diode laser or a fiber laser. Any known technique may be used to stabilize the output wavelength of the seed laser 202, such as distributed feedback, a fiber-Bragg grating, or an etalon. In preferred embodiments, the Raman amplifier 204 amplifies the mW-level light from the seed laser 202 to the 1109 nm light 205 at a power level of between about 1 W and 20 W.

In other embodiments (not shown) of the 1109 nm generator 200, no seed laser is used. Instead, the Raman amplifier is operated as a Raman laser or oscillator with frequency selective elements incorporated so as to limit the bandwidth and control the output wavelength.

Figure 2B:
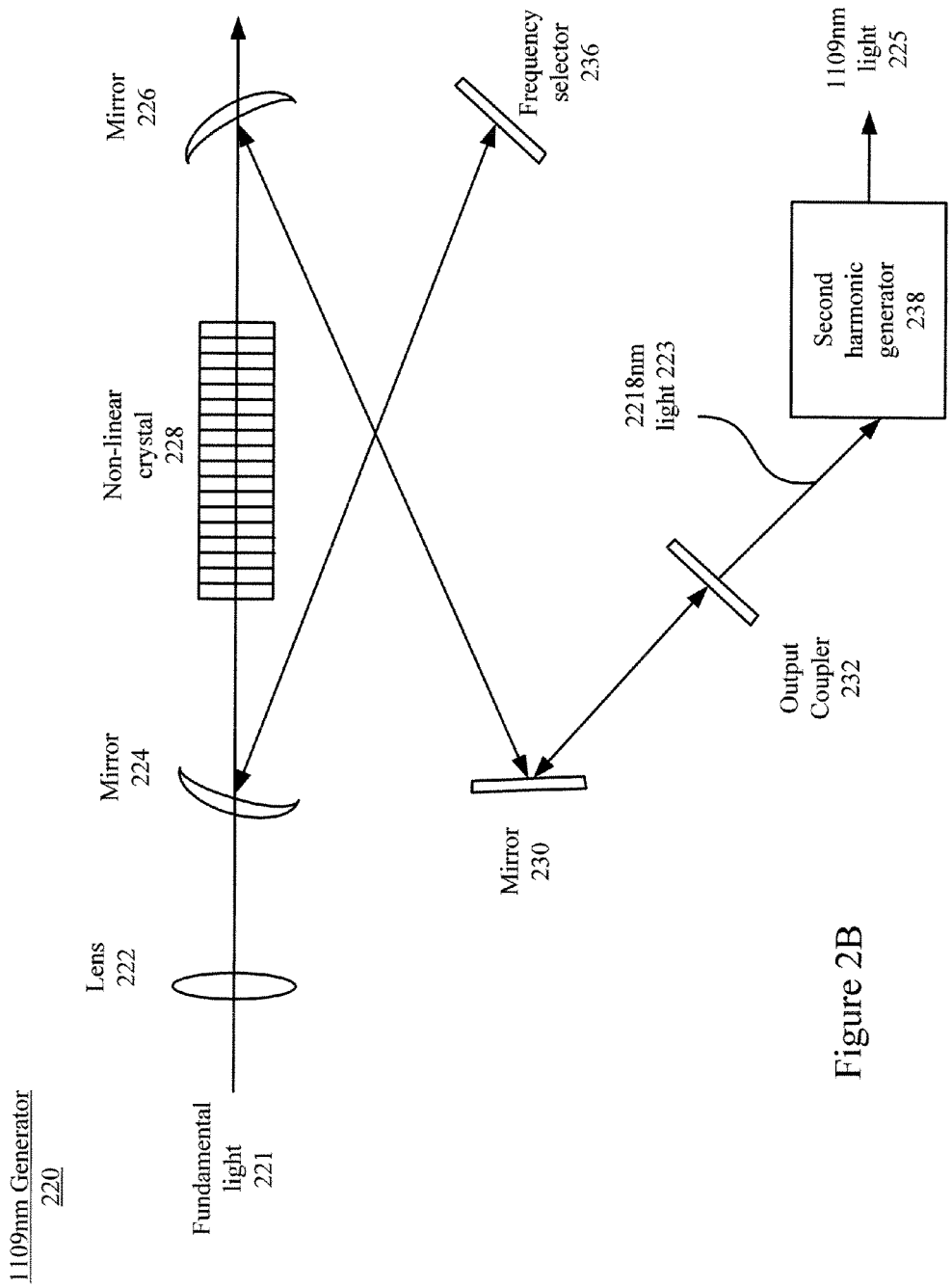
FIG. 2B illustrates a block diagram of an alternative exemplary generator for generating a wavelength of approximately 1109 nm.

FIG. 2B illustrates a simplified block diagram of an alternative exemplary embodiment of an 1109 nm generator 220 that can perform the functions of the 1109 nm generator 108 (FIG. 1A) and the 1109 nm generator 128 (FIG. 1B). In this embodiment, a 1109 nm light 225 at a wavelength is generated from a fundamental light 221 using a non-linear crystal 228 to generate a light 223 at a wavelength twice equal to twice the desired wavelength (i.e. a wavelength of approximately 2218 nm), which is then doubled in frequency by a second harmonic generator 238 to generate the 1109 nm light 225 at the desired wavelength. The second harmonic generator 238 may use KTP, LNB (lithium niobate), or another non-linear crystal.

The fundamental light 221 is focused by a lens 222 and directed into an optical cavity formed by curved mirrors 224 and 226, a frequency selector 236, a flat mirror 230, and an output coupler 232. In one embodiment (shown), the optical cavity further includes a non-linear crystal 228 comprising a material such as LNB, doped LNB, lithium tantalate, magnesium-doped lithium tantalate or KTP. In some embodiments, the non-linear crystal 228 may be periodically-poled. The curved mirrors 224 and 226 are coated with a coating that is highly reflective for light with a wavelength near 2218 nm, but is substantially transparent to wavelengths near the fundamental wavelength and the idler wavelength which is near 2 μm in wavelength (the exact wavelength depends on the fundamental wavelength, and will typically be in range between about 1980 nm and about 2050 nm). Note that in this configuration, the desired (signal) wavelength is longer than the unwanted (idler) wavelength. The frequency selector 236 is highly reflective in a narrow band centered on the desired output wavelength near 2218 nm, but has high transmission for other wavelengths close to the desired wavelength. The frequency selector 236 determines the wavelength and bandwidth of the optical parametric oscillator. In preferred embodiments, the bandwidth is less than 1 nm, such as a few tenths of a nanometer. The frequency selector 236 may comprise a volume-Bragg grating, a birefringent filter, a notch filter, or an etalon. The frequency selector 236 may operate in reflection as shown, or a transmissive frequency-selective element may be placed at an appropriate location in the optical cavity with the frequency selector 236 acting as a reflector or mirror.

The output coupler 232 transmits a fraction (such as approximately 50%, or between about 5% and 95%) of the incident light at the output wavelength to the second harmonic generator 236. Light at the output wavelength not transmitted by the output coupler 232 is reflected back into the optical cavity. Mirror 230 serves to direct the output light in the correct direction. In one embodiment, mirror 230 may not be required. In another embodiment, multiple mirrors may be used instead of mirror 230. In yet another embodiment, one or more prisms may be instead of the mirror 230.

Figure 2C:
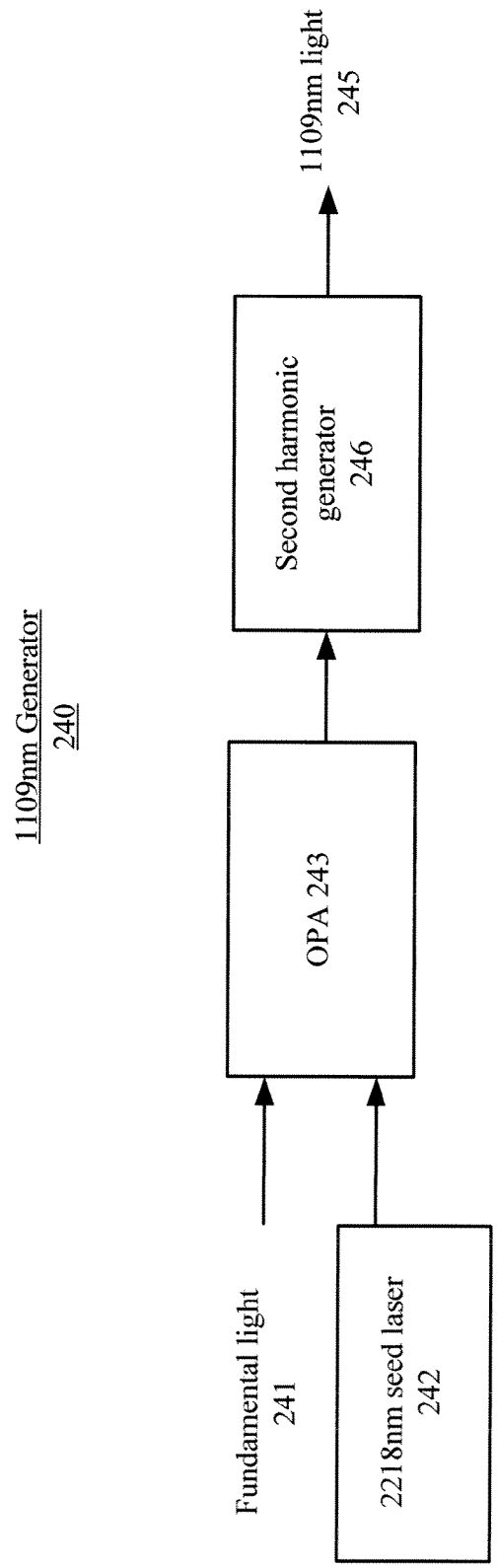
FIG. 2C illustrates a block diagram of another alternative exemplary generator for generating a wavelength of approximately 1109 nm.

FIG. 2C illustrates a simplified block diagram of an alternative exemplary embodiment of an 1109 nm generator 240 that can perform the functions of the 1109 nm generator 108 (FIG. 1A) and the 1109 nm generator 128 (FIG. 1B). In this embodiment, a 2218 nm seed laser 242 is used to generate a low-power signal of the desired wavelength and bandwidth that is input into an optical parametric amplifier (OPA) 243 along with a portion of a fundamental light 241. The OPA 243 operates in a similar manner to the configuration described with respect to FIG. 2B, but it does not need a narrow-band wavelength selective element (such as a volume Bragg grating), because the 2218 nm seed laser 242 determines the wavelength and bandwidth. The OPA 243 may use a similar non-linear crystal, such as LNB, lithium tantalate or KTP (bulk or periodically poled) as described above. The output of the OPA 243 is directed to a second harmonic generator 246, which generates a desired 1109 nm light 245. The second harmonic generator 246 may be configured similarly to the second harmonic generator 236 (FIG. 2B).

Figure 3:
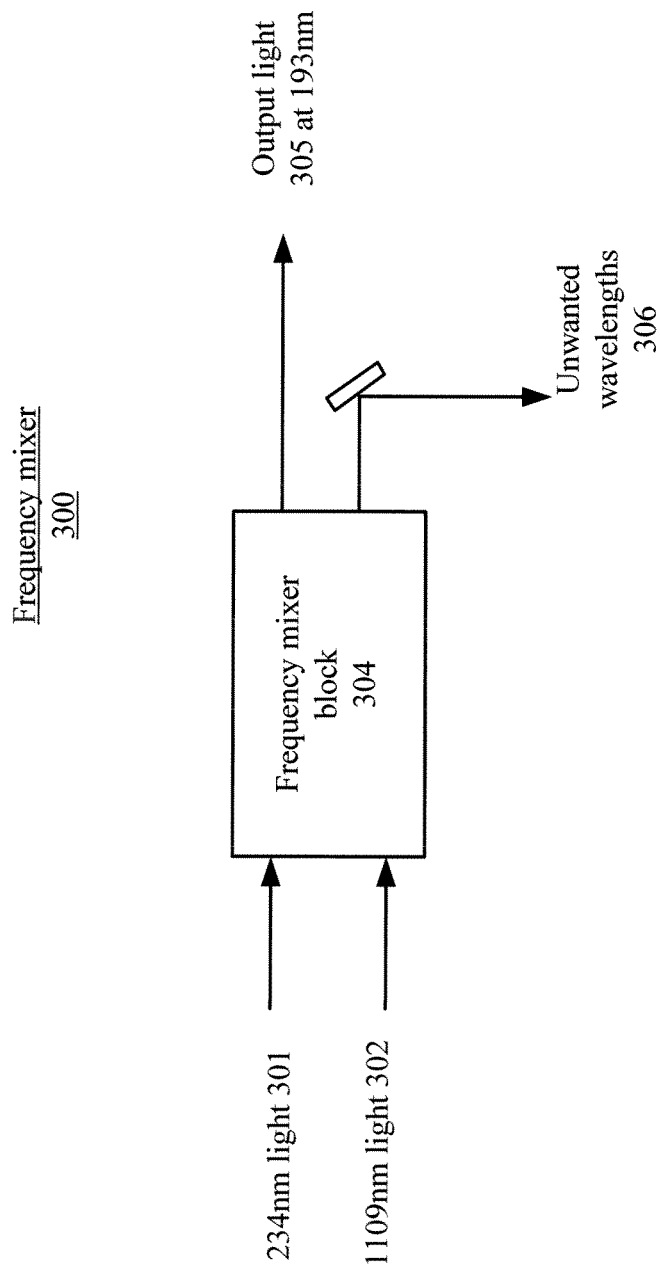
FIG. 3 illustrates a block diagram of an exemplary frequency mixer for generating 193 nm light by mixing a wavelength near 1109 nm with a wavelength near 234 nm.

FIG. 3 shows an illustrative block diagram of an exemplary embodiment of a frequency mixer 300 that creates an output light 305 at a wavelength near 193 nm, such as a wavelength of substantially 193.4 nm. Frequency mixer 300 can perform the function of frequency mixer 110 (FIG. 1A) and of frequency mixer 130 (FIG. 1B). In this embodiment, a 234 nm light 301, such as a wavelength near 234.2 nm, is mixed in a frequency mixer block 304 with a 1109 nm light 302 to create the output light 305. The frequency mixer block 304 may include a non-linear crystal, such as CLBO or BBO as described above. In preferred embodiments, the non-linear crystal is kept in a controlled environment to maintain a constant temperature and protect the crystal from humidity and contaminants. Details of such protective environments can be found in U.S. Pat. No. 8,298,335 by Armstrong, which issued on Oct. 30, 2012, and is incorporated by reference herein. In this embodiment, any unconsumed input light 306 is separated from the output light 305 using prims, polarizing beam splitters, or other means.

Figure 4A:
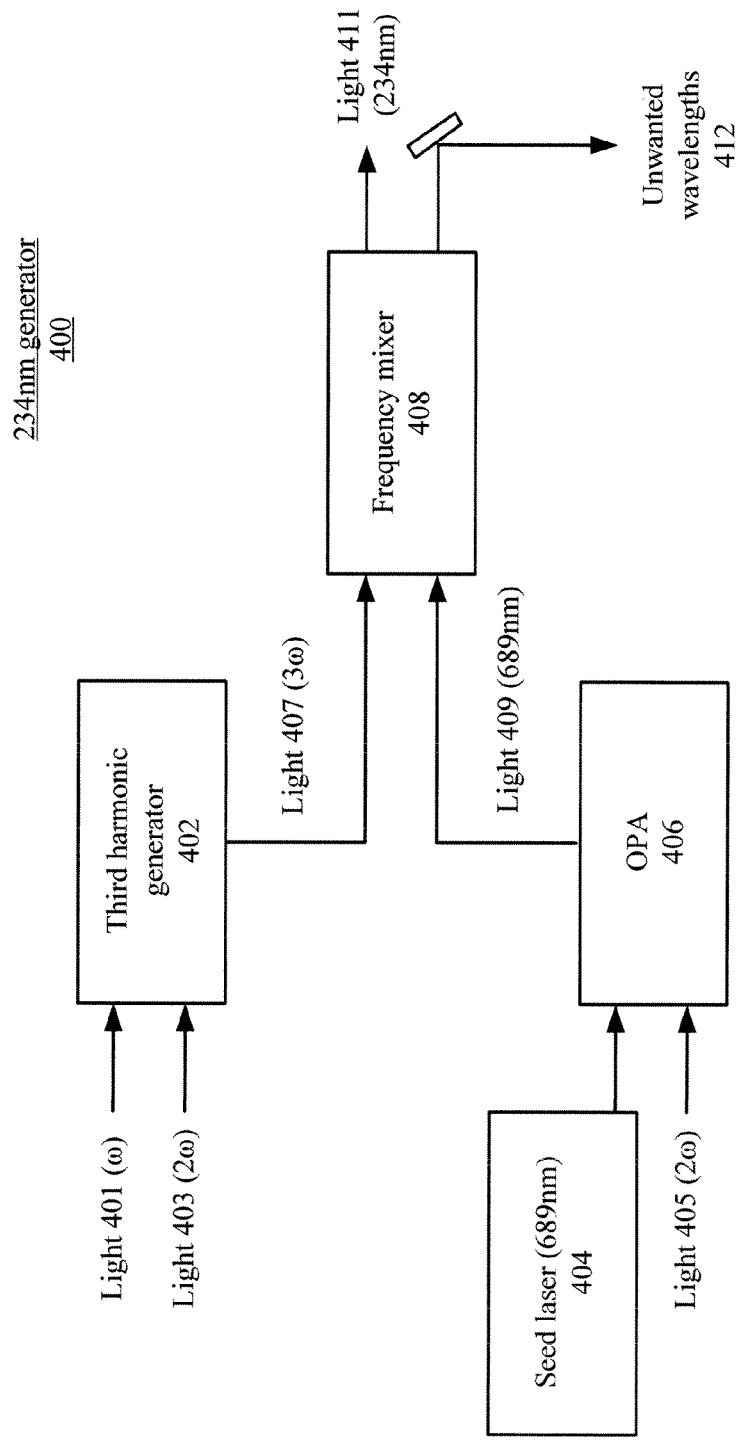
FIG. 4A illustrates a block diagram of an exemplary generator that generates a wavelength of approximately 234 nm from the fundamental and second harmonic.

FIG. 4A shows an illustrative block diagram of an exemplary embodiment of the 234 nm generator 400 that creates light 411 at a wavelength near 234 nm, such as a wavelength of substantially 234.2 nm. The 234 nm generator 400 can perform the function of the frequency conversion stages 106 of FIG. 1A.

The 234 nm generator 400 uses a third-harmonic generator 402 to create a third harmonic 407 by combining a portion 401 of the fundamental frequency with the second harmonic 403. If the fundamental wavelength is close to 1064 nm, then the third harmonic will have a wavelength close to 355 nm. If the fundamental is close to 1053 nm, then the third harmonic will have a wavelength close to 351 nm. If the fundamental is close to 1047 nm, then the third harmonic will have a wavelength close to 349 nm. The third harmonic generator 402 includes a non-linear crystal such as CLBO, BBO or LB4. The fundamental 401 and the second harmonic 403 can be taken from the output of the second harmonic generator 104 shown in FIG. 1A.

Another portion 405 of the fundamental frequency is used by an optical parametric amplifier or optical parametric oscillator 406 to generate light 409 at a wavelength of approximately 689 nm. The light 409 at a wavelength of approximately 689 nm is mixed with the third harmonic 407 in the frequency mixer 408 to generate the output light 411 at a wavelength near 234 nm. Unconsumed third harmonic and 689 nm light can be separated from the output of the frequency mixer 408 and discarded as 412. The portion 405 of the fundamental can be taken from the output of the second harmonic generator 104, from the output of the third harmonic generator 402, from the output of the 1109 nm generator 108, directly from the fundamental laser 102, or any other convenient place.

The exact wavelength of the light 409 at approximately 689 nm should be chosen so as to generate the desired output wavelength at 411. For example, in preferred embodiments, the output wavelength 411 is substantially 234.2 nm. In such embodiments, if, for example, the fundamental is close to 1064.4 nm, then the light 409 should have a wavelength of substantially 689.0 nm. If the fundamental is close to 1053.0 nm, then the light 409 should have a wavelength close to 703.8 nm. If the fundamental is close to 1047.0 nm, then the light 409 should have a wavelength close to 712.0 nm.

In some embodiments, a seed laser diode 404 at the desired wavelength of approximately 689 nm, such as a wavelength near 689.0, 703.8 or 712.0 nm, with the desired bandwidth and stability is used to seed the optical parametric amplifier or 406. In other embodiments, wavelength selective elements such as a volume Bragg grating, or a diffraction grating, is used to determine the center wavelength and bandwidth of the optical parametric amplifier or optical parametric oscillator 406.

Figure 4B:
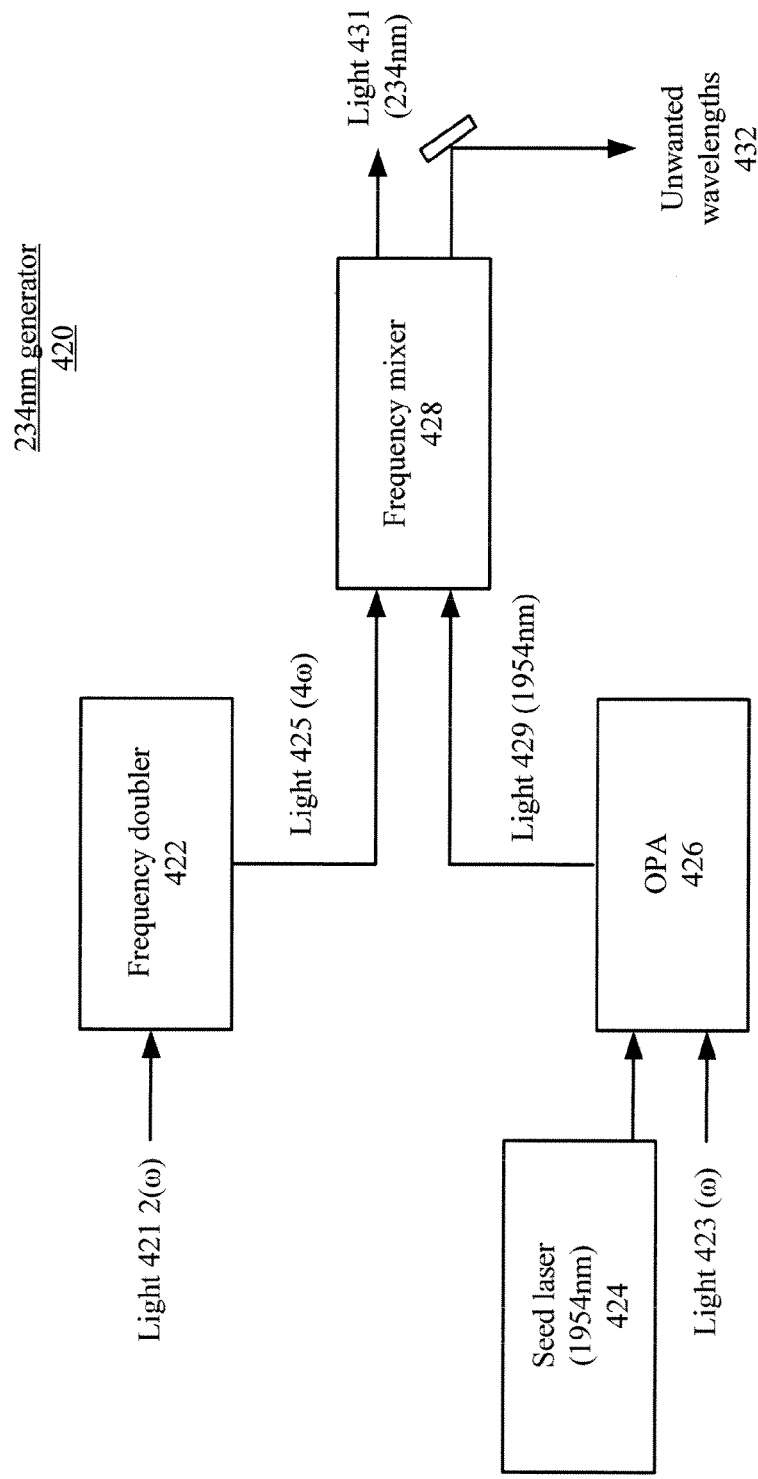
FIG. 4B illustrates a block diagram of an alternative exemplary generator that generates a wavelength of approximately 234 nm from the fundamental and second harmonic.

FIG. 4B shows an illustrative block diagram of an alternative exemplary embodiment of the 234 nm generator 420 that creates light 431 at a wavelength near 234 nm, such as a wavelength of substantially 234.2 nm. The 234 nm generator 420 can perform the function of the frequency conversion stages 106 of FIG. 1A.

The 234 nm generator 420 creates a fourth harmonic 425 from the second harmonic 421 in the frequency doubler 422. If the fundamental wavelength is close to 1064 nm, then the fourth harmonic will have a wavelength close to 266 nm. If the fundamental is close to 1053 nm, then the fourth harmonic will have a wavelength close to 263.3 nm. If the fundamental is close to 1047 nm, then the fourth harmonic will have a wavelength close to 261.8 nm. The frequency doubler 422 includes a non-linear crystal such as CLBO, BBO or LB4. The second harmonic 421 can be taken from the output of the second harmonic generator 104 shown in FIG. 1A.

A portion 423 of the fundamental frequency is used by an optical parametric amplifier or optical parametric oscillator 426 to generate light 429 at a wavelength of approximately 1954 m. The light 429 at a wavelength of approximately 1954 nm is mixed with the fourth harmonic 425 in the frequency mixer 428 to generate the output light 431 at a wavelength near 234 nm. Any unconsumed fourth harmonic and approximately 1954 nm light can be separated from the output of the frequency mixer 428 and discarded as 432. The portion 423 of the fundamental can be taken from the output of the second harmonic generator 104, from the output of the 1109 nm generator 108, directly from the fundamental laser 102, or any other convenient place.

The exact wavelength of the light 429 at approximately 1954 nm should be chosen so as to generate the desired output wavelength at 431. For example, in preferred embodiments, the output wavelength 411 is substantially 234.2 nm. In such embodiments, if, for example, the fundamental is close to 1064.4 nm, then the light 429 should have a wavelength of substantially 1954 nm. If the fundamental is close to 1053.0 nm, then the light 409 should have a wavelength close to 2122 nm. If the fundamental is close to 1047.0 nm, then the light 409 should have a wavelength close to 2225 nm.

In some embodiments, a seed laser diode 424 at the desired wavelength of approximately 1954 nm, such as a wavelength near 1954, 2122 or 2225 nm, with the desired bandwidth and stability is used to seed the optical parametric amplifier or optical parametric oscillator 426. In other embodiments, wavelength selective elements such as a volume Bragg grating, or a diffraction grating, is used to determine the center wavelength and bandwidth of the optical parametric amplifier or optical parametric oscillator 426.

Figure 5A:
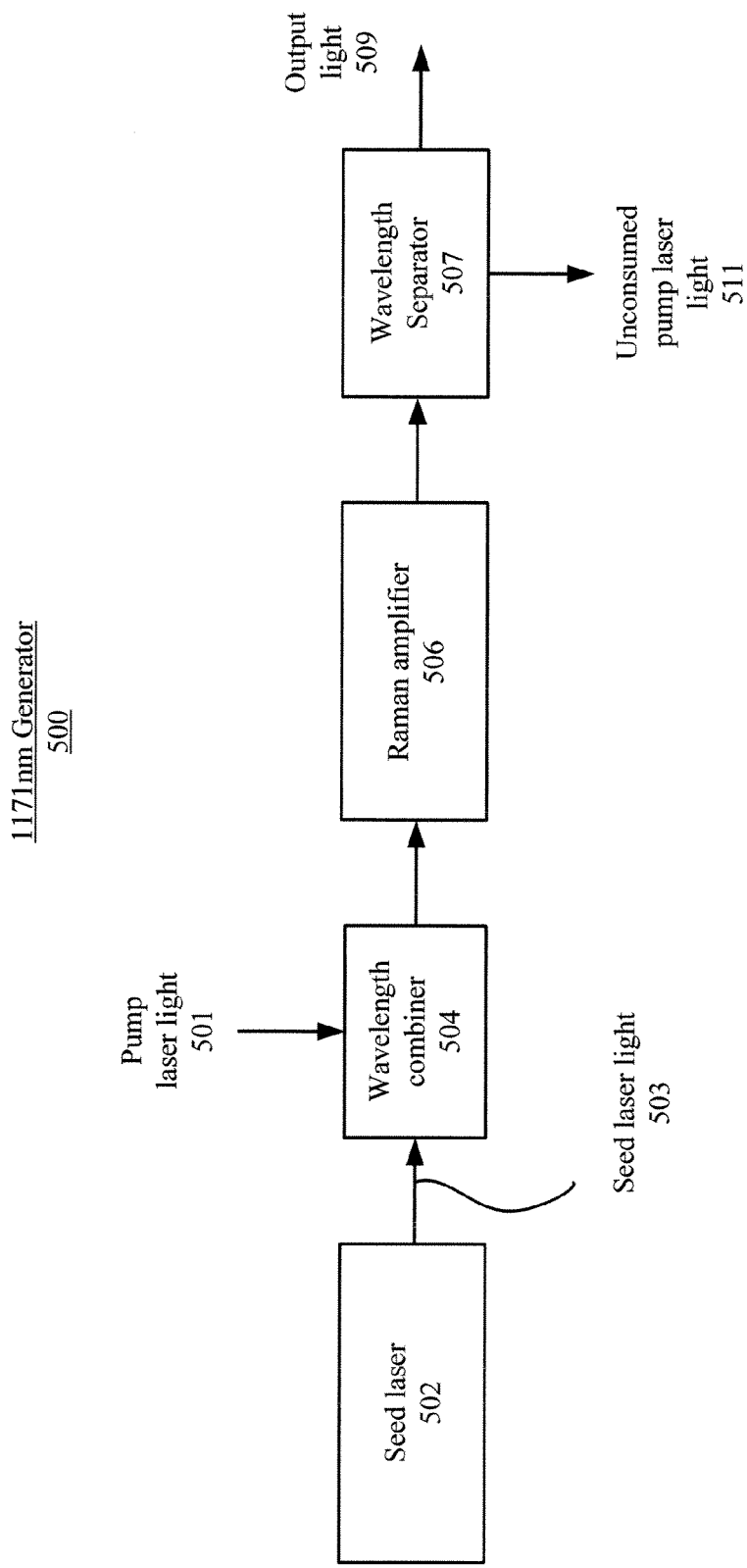
FIG. 5A illustrates an exemplary generator for generating a wavelength near 1171 nm.

FIG. 5A shows an illustrative block diagram of an exemplary embodiment of the 1171 nm generator 500 that creates light 509 at a wavelength near 1171 nm. The 1171 nm generator 500 can perform the function of the 1171 nm generator 124 of FIG. 1B or the 1171 nm generator 144 of FIG. 1C. The 1171 nm generator 500 generates the output light 509 by amplifying seed laser light 503 with desired center wavelength (near 1171 nm) and bandwidth. The amplification is performed by a Raman amplifier 506. The Raman amplifier may comprise a fused silica fiber or may comprise a germania-doped fused silica fiber. A stable seed laser 502, such as a frequency-stabilized laser diode or low-power fiber laser generates the seed laser light 503. In some embodiments, the seed laser 502 may generate a power between about 1 mW and 250 mW. The seed laser 502 may be a CW laser, or may be a pulsed laser that is synchronized with the fundamental laser. The seed laser light 503 is combined with the pump laser light 501 by a wavelength combiner 504. The pump laser light 501 may comprise light at a wavelength near 1109 nm or may comprise the fundamental wavelength and may, for example, be taken from the output of, or unconsumed fundamental from, the 1109 nm generator 128 in FIG. 1B, the 1109 nm generator 148 in FIG. 1C, or directly from the fundamental laser 122 (FIG. 1B) or 142 (FIG. 1C). The pump laser light 501 may also be taken from unconsumed 1109 nm light 129' from the frequency mixer 130 as shown in FIG. 1B. As described above, the second-order Raman shift of fused silica may be efficiently used with a pump wavelength near 1064 nm or near 1053 nm. The wavelength separator 507 separates unconsumed pump laser light 511 from the output light 509. The unconsumed pump laser light 511 may be used as an input to another stage, or may be dumped.

Figure 5B:
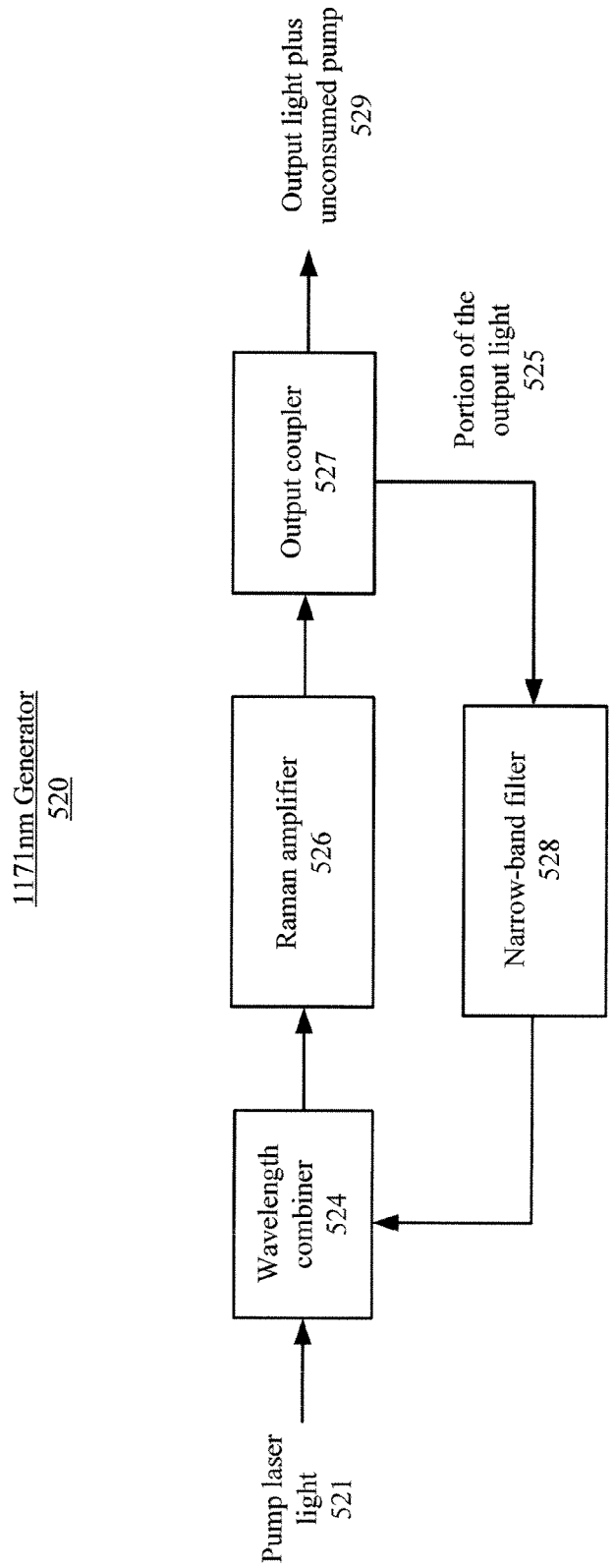
FIG. 5B illustrates an alternative exemplary generator for generating a wavelength near 1171 nm.

FIG. 5B shows an illustrative block diagram of an alternative exemplary embodiment of the 1171 nm generator 520 that creates light 529 at a wavelength near 1171 nm. The 1171 nm generator 520 can perform the function of the 1171 nm generator 124 of FIG. 1B or the 1171 nm generator 144 of FIG. 1C. The 1171 nm generator 520 generates the output light 529 at a wavelength near 1171 nm using a fiber optical parametric oscillator that includes a Raman amplifier. The amplification is performed by a Raman amplifier 526, which generates a first-order or second-order Raman shift from the pump wavelength in a fused silica or gemania-doped fused silica fiber in manner similar to that just described for FIG. 5A. A portion 511 of the output wavelength near 1171 nm is fed back by an output coupler 527. In preferred embodiments between about 1% and about 50% of the output wavelength may be fed back. A narrow-band filter 528, such as a fiber Bragg grating, selects the wavelength and bandwidth to feedback and hence determines the wavelength and bandwidth of the output. The portion 511 of the output light that is fed back is combined with the pump laser light 521 by the wavelength combiner 524. The pump laser light 501 is light at a wavelength of approximately 1109 nm or at the fundamental wavelength and may, for example, be taken from the output of, or unconsumed fundamental from, the 1109 nm generator 128 in FIG. 1B, the 1109 nm generator 148 in FIG. 1C, or directly from the fundamental laser 122 (FIG. 1B) or the fundamental laser 142 (FIG. 1C). As described above, the second-order Raman shift of fused silica may be efficiently used with a pump wavelength near 1064 nm or near 1053 nm. The output is a mixture of the output light at a wavelength near 1171 nm and unconsumed pump wavelength. Those wavelengths may be separated if desired. The 1171 nm generator 520 can be built entirely from fiber-optic based components. This can be particularly advantageous if the fundamental laser is a fiber laser.

Figure 6A:
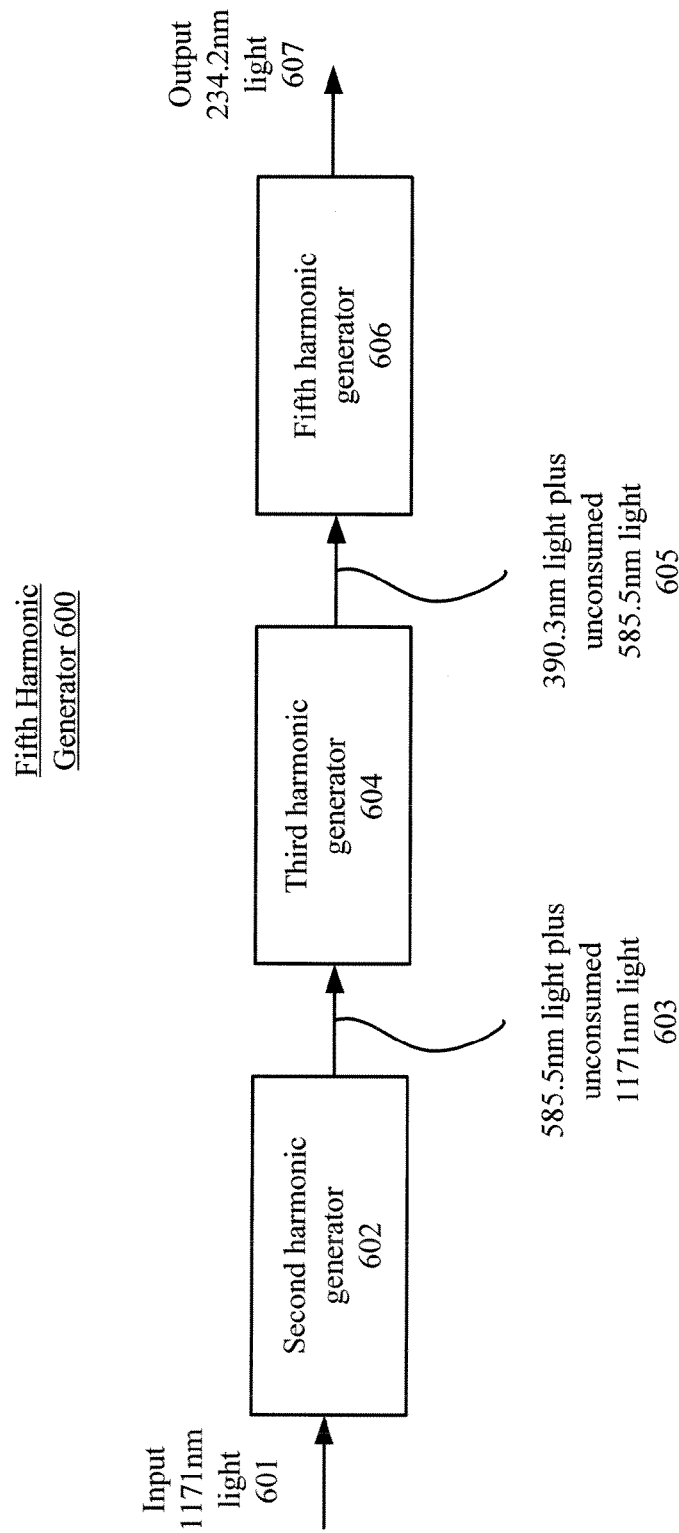
FIG. 6A illustrates an exemplary $5^{th}$ harmonic generator for generating the $5^{th}$ harmonic of a wavelength of approximately 1171 nm.

FIG. 6A shows an illustrative block diagram of an exemplary preferred embodiment of the fifth harmonic generator 600 that creates output light 607 at a wavelength near 234 nm, such as a wavelength of substantially 234.2 nm, from the input light 601 at a wavelength of 1171 nm. Fifth harmonic generator 600 generates the fifth harmonic 607 by first generating the second harmonic at a wavelength of 585.5 nm in a second harmonic generator 602. The second harmonic generator 602 includes a non-linear crystal, preferably LBO, which is phase-matched for generating the second harmonic at an angle of about 83° at a temperature of about 120° C. with a low walk-off angle of about 6 mrad. The output 603 of the second harmonic generator 602 includes both unconsumed 1171 nm light and the second harmonic at a wavelength of 585.5 nm.

The output 603 of the second harmonic generator 602 is passed to the third harmonic generator 604 that creates the third harmonic by mixing the 1171 nm wavelength with the second harmonic at 585.5 nm. The third harmonic generator 604 includes a non-linear crystal, CLBO in one preferred embodiment, which is phase-matched for generating the third harmonic at an angle of about 77.5° at a temperature of about 120° C. with a walk-off angle of about 15 mrad. The output 605 of the third harmonic generator 604 includes unconsumed 1171 nm and 585.5 nm light and the third harmonic at a wavelength close to 390.3 nm. Any unconsumed 1171 nm light may be separated from the output or may be passed to the next stage if it will not cause any problems.

The output 605 of the third harmonic generator 604 is passed to the fifth harmonic generator 606 that creates the fifth harmonic 607 by mixing the 585.5 nm wavelength second harmonic with the 390.3 nm wavelength third harmonic. The fifth harmonic generator 606 includes a non-linear crystal, preferably CLBO, which is phase-matched for generating the fifth harmonic at an angle of about 86.4° at a temperature of about 120° C. with a walk-off angle of about 5 mrad. Any unconsumed 1171 nm, 585.5 nm or 390.3 nm light may be separated or filtered from the output 607.

Figure 6B:
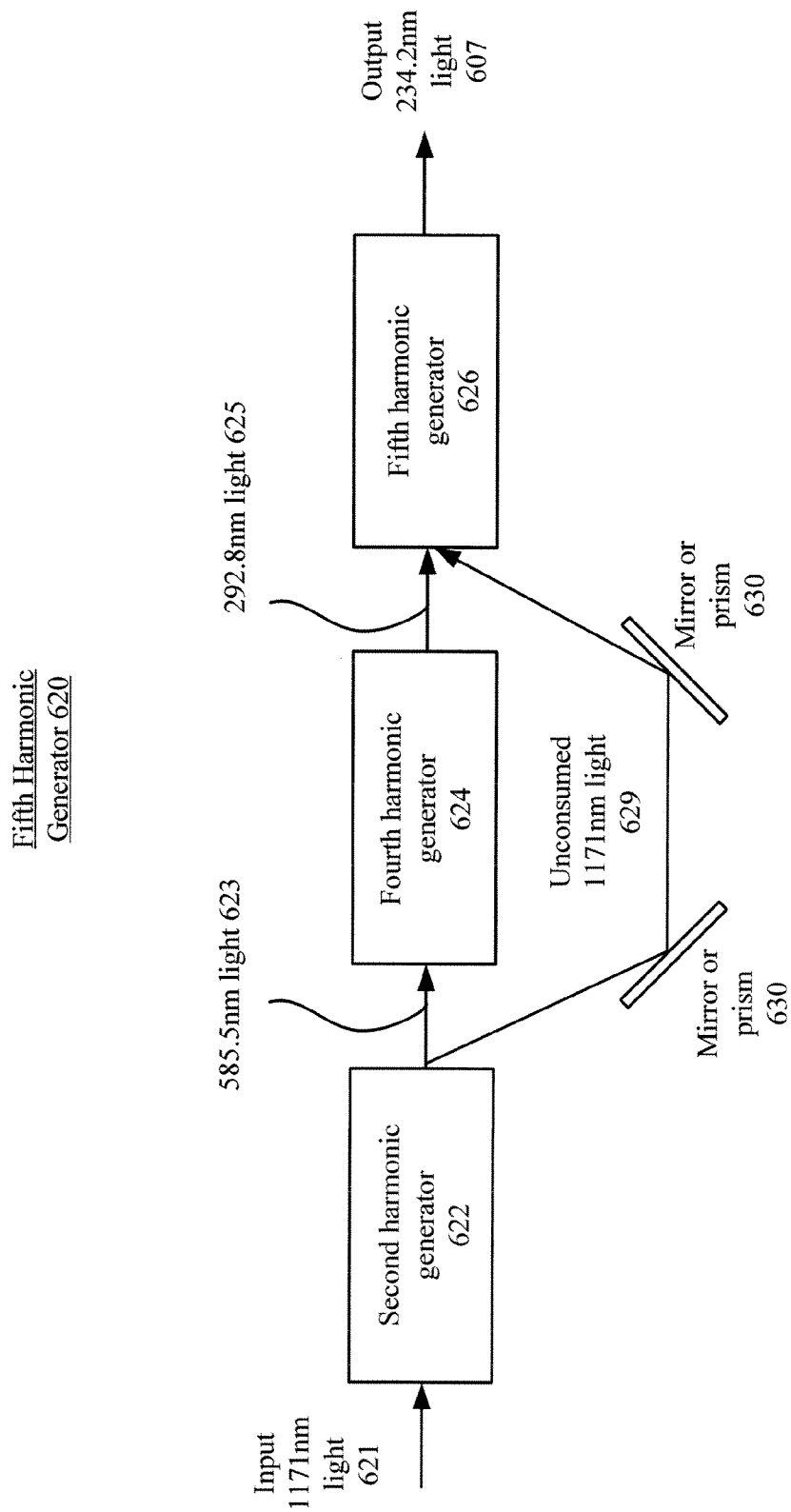
FIG. 6B illustrates an alternative exemplary $5^{th}$ harmonic generator for generating the $5^{th}$ harmonic of a wavelength of approximately 1171 nm.

FIG. 6B shows an illustrative block diagram of an alternative exemplary embodiment of the fifth harmonic generator 620 that creates output light 627 at a wavelength near 234 nm, such as a wavelength of substantially 234.2 nm from the input light 601 at a wavelength of 1171 nm. Fifth harmonic generator 620 generates the fifth harmonic 627 by first generating the second harmonic at a wavelength of 585.5 nm in a second harmonic generator 622 that functions substantially similarly to second harmonic generator 602 of FIG. 6A. The unconsumed 1171 nm light 629 at the output of the second harmonic generator 622 may be separated from the second harmonic 623 and directed to the fifth harmonic generator 626 using, for example, mirrors and/or prisms such as those labeled 630. In some embodiments, it may be possible to pass the unconsumed 1171 nm light 629 through the fourth harmonic generator 624 because it is not phase matched and does not significantly interfere with the frequency conversion.

The second harmonic 623 at a wavelength of 585.5 nm is passed to fourth harmonic generator 624. Fourth harmonic generator 624 includes a non-linear crystal such as CLBO, BBO or KDP (potassium dihydrogen phosphate). Fourth harmonic generator 624 creates the fourth harmonic 625 at a wavelength of 292.8 nm. Unconsumed second harmonic may be separated from the output of the fourth harmonic generator 624.

The fourth harmonic 625 is passed to the fifth harmonic generator 626 which combines it with light at 1171 nm to create the fifth harmonic output 627 at a wavelength near 234.2 nm. Unconsumed light at 1171 nm or 292.8 nm may be separated or filtered from the output. The fifth harmonic generator 626 includes a non-linear crystal such as KDP, CLBO, BBO or LB4.

Figure 7:
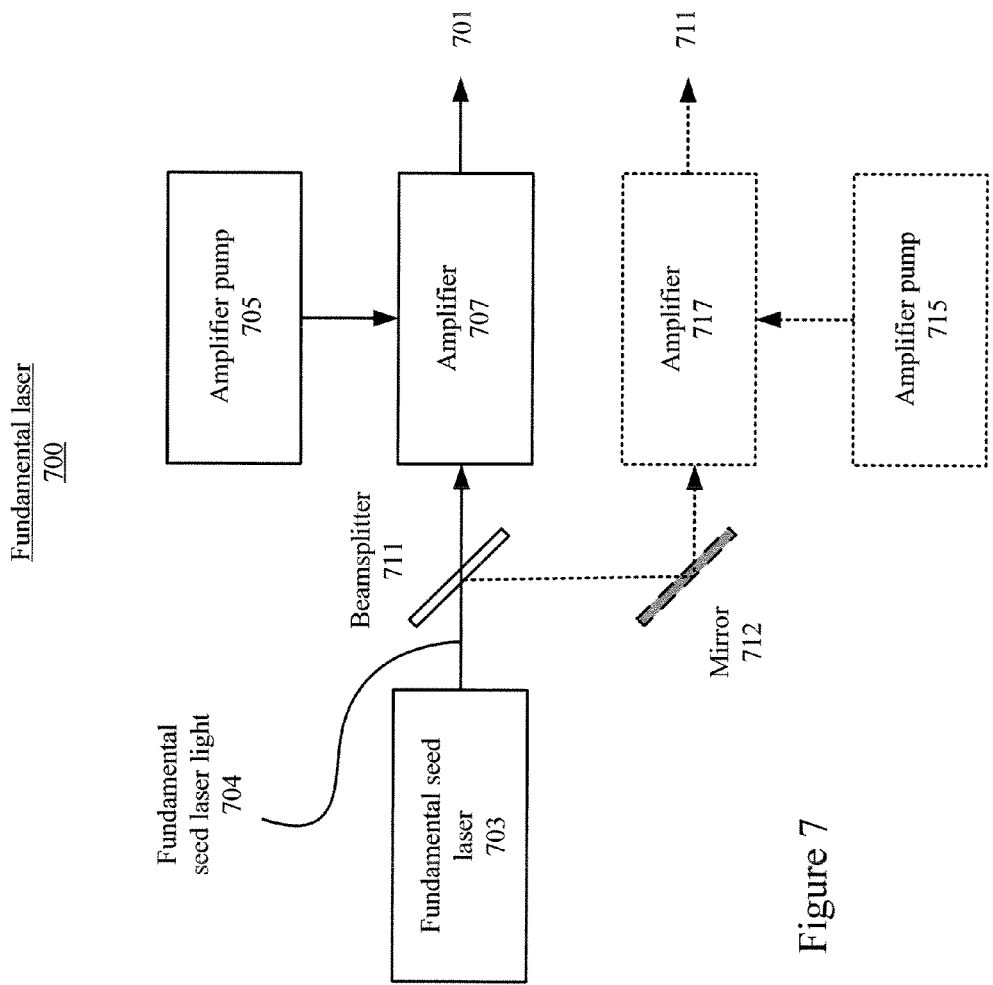
FIG. 7 illustrates an exemplary embodiment of the fundamental laser.

In some embodiments, to generate sufficient power at the fundamental wavelength, two or more amplifiers may be used. Note that if two or more amplifiers are used, then one seed laser should preferably be used to seed all the amplifiers so that the outputs from all amplifiers are at the same wavelength and are synchronized one with another. This is illustrated by the block diagram 700 in FIG. 7. Multiple amplifiers are advantageous when a single amplifier cannot easily be made to operate at the desired power level with the required bandwidth due to effects such as thermal lensing, self-phase modulation, or cross-phase modulation, or in cases where the heat dissipated in a single amplifier makes cooling that amplifier difficult or expensive.

The seed laser 703 generates light at the desired fundamental wavelength with the right bandwidth near 1064 nm, 1053 nm or 1047 nm. The seed laser (or oscillator) may be a diode laser, an Nd-doped yttrium orthovanadate laser, an Nd:YAG laser, an Nd:YLF laser or a fiber laser. In one embodiment, the output of the seed laser 704 is divided by beam splitter 711 and is directed to two or more amplifiers such as 707 and 717. Each amplifier outputs light (701 and 711 respectively) at the fundamental wavelength, but at a higher power than the output of the seed laser 703. Mirrors and/or prisms such as 712 may be used as needed to direct the fundamental seed light 704 to the different amplifiers such as 707 and 717. Each amplifier has its own pump (shown as 705 and 715), which, preferably, comprises laser diodes.

Any of the harmonic generators or frequency mixers may use some, or all, of the methods and systems disclosed in U.S. patent application Ser. No. 13/412,564, entitled "Laser With High Quality, Stable Output Beam, And Long Life High Conversion Efficiency Non-Linear Crystal", by Dribinski et al., filed Mar. 5, 2012 and incorporated by reference herein. Any of the harmonic generators or frequency mixers, particularly those generating UV wavelengths, may advantageously use hydrogen-annealed non-linear crystals. Such crystals may be processed as described in U.S. patent application Ser. No. 13/488,635, entitled "Hydrogen Passivation of Nonlinear Optical Crystals" by Chuang et al., filed on Jun. 1, 2012, which is incorporated by reference herein.

Any of the frequency conversion, harmonic generation, or frequency mixing stages may be in a protected environment, such as the protected environment described in the '335 patent. This protected environment is particularly useful in protecting stages that use or generate wavelengths shorter than about 300 nm, since such wavelengths can easily cause photocontamination of optical surfaces. The protected environment is also very useful for stages that include a hygroscopic material such as CLBO, LBO or BBO. A single protective environment may protect just one stage, or may protect multiple stages.

As known by those skilled in the art, mirrors, or prisms may be used to direct the light where needed. Lenses and curved mirrors may be used to focus the beam waist to a point inside or proximate to the non-linear crystals where appropriate. Prisms, gratings, beam splitters, or diffractive optical elements may be used to separate the different wavelengths at the outputs of each harmonic generator module when needed. Prisms, beam splitters, diffractive optical elements, or dichroic mirrors may be used to combine wavelengths where needed. Beam splitters or coated mirrors may be used as appropriate to divide one wavelength into two beams.

Note that these techniques and additional details are exemplary and any laser constructed in accordance with this application may vary based on implementation and/or system constraints. Multiple embodiments are described above illustrating several variations and equivalents of this approach for generating light near 193 nm. When a sub-200 nm wavelength is required, such as a wavelength in the range from approximately 190 nm to approximately 200 nm, but not substantially 193.4 nm, small changes could be made to one or more of the wavelengths generated by optical parametric or Raman shift amplifiers without departing from the scope of this invention. One skilled in the relevant arts will appreciate that different, but substantially equivalent, frequency conversion techniques may be used without departing from the scope of the invention. Any embodiment might use multiple crystals in a walkoff-compensation geometry to improve the frequency conversion efficiency and beam profile in any critically phase matched stage.

Figure 8:
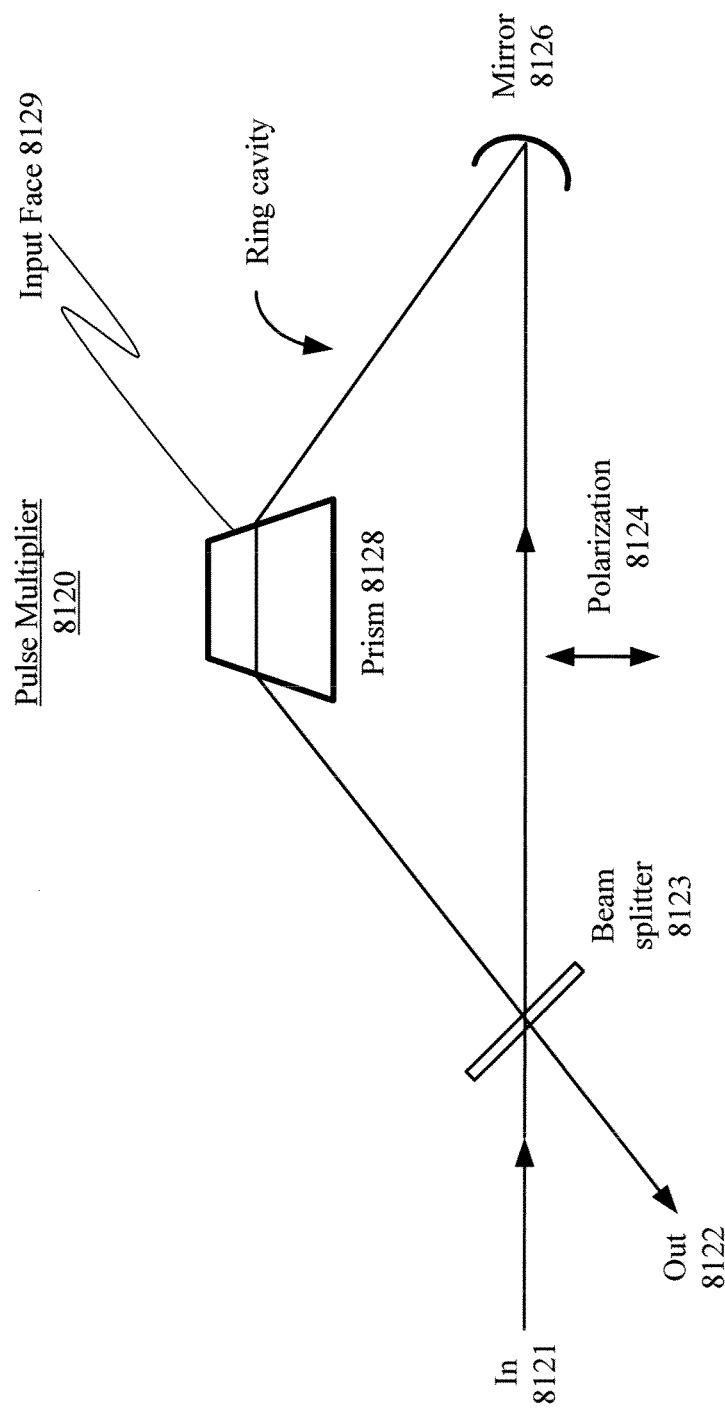
FIG. 8 illustrates an exemplary pulse multiplier that may be used in combination with the sub-200 nm laser and an inspection or metrology system.

FIG. 8 illustrates an exemplary pulse multiplier 8120 that may be used with any of the above described laser embodiments to increase the pulse repetition rate in a metrology or inspection system. Increasing the repetition rate of the fundamental laser while maintaining the pulse width and maintaining constant average output power would result in reduced peak power and, hence, lower efficiency from the frequency conversion and mixing stages. The pulse multiplier 8120 overcomes this problem by leaving the fundamental laser repetition rate unchanged and dividing each output pulse into multiple pulses, thus increasing the repetition rate without reducing the efficiency of the frequency conversion and mixing stages.

Pulse multiplier 8120 is configured to generate pulse trains from each input pulse. Input pulses at a wavelength of approximately 193 nm arrive from direction 8121 and impinge on a beam splitter 8123, which reflects part of each pulse in an output direction 8122, and transmits part into a ring cavity towards a mirror 8126. The input and output pulses are substantially polarized in a direction parallel to the arrow 8124. Thus, the output polarization is substantially parallel to the input polarization.

The ring cavity includes a mirror 8126, a prism 8128, and the beam splitter 8123. The mirror 8126 refocuses the light circulating within the ring cavity. Preferably, the radius of curvature of the mirror 8126 is substantially equal to half of the optical path length of the ring cavity so that the beam waist is refocused with a magnification of one each trip around the ring cavity. Brewster's angle cuts are preferably used for the input and output faces of the prism 8128, thereby minimizing or largely eliminating reflection losses at those faces (the input face of prism 8128 is labeled 8129) because the light incident on the face of the prism 8128 is substantially p polarized relative to that face. After light exits the prism 8128, it is directed back to the beam splitter 8123, where part of each pulse is transmitted through the beam splitter 8123 in the output direction 8122, and part is reflected back into the ring cavity.

Details of this pulse multiplier and alternative pulse multiplier configurations are described in copending U.S. patent application Ser. No. 13/711,593, entitled "SEMICONDUCTOR INSPECTION AND METROLOGY SYSTEM USING LASER PULSE MULTIPLIER", by Chuang et al., filed on Dec. 11, 2012 and claiming priority to U.S. Provisional Application 61/733,858, entitled "Semiconductor Inspection And Metrology System Using Laser Pulse Multiplier", and filed on Dec. 5, 2012, and in copending U.S. patent application Ser. No. 13/487,075 entitled "Semiconductor Inspection And Metrology System Using Laser Pulse Multiplier", filed on Jun. 1, 2012 by Chuang et al. and claiming priority to U.S. Provisional Application 61/496,446, filed on Jun. 13, 2011 by Chuang et al. These applications are incorporated by reference herein.

As described in the '593 application, the optical path length of the ring cavity may be set to be approximately equal to an integer fraction of the distance between successive incoming pulses, where the distance between two pulses is equal to the velocity of light multiplied by the time interval between those pulses. For example, in some embodiments the optical path length of the cavity may be set to be approximately one half of the distance between the incoming pulses. For such a ring cavity, every second pulse will approximately coincide with an arriving input pulse, thus doubling the repetition rate. The '593 application also describes how the optical cavity length may be set slightly longer or slightly shorter than half of the distance between incoming pulses so as to further reduce the peak power of the output pulses.

The '593 application describes how, in preferred embodiments, the beam splitter 8123 reflects approximately one third of the energy of each incident pulse and transmits approximately two thirds of the energy of each incident pulse so as to generate an output stream of substantially equal energy pulses in a pulse rate doubler. This application further describes how to adjust the transmission and reflection ratios of the beam splitter 8123 in order to achieve substantially equal output pulse energies in the presence of beam splitter and cavity losses.

Figure 9:
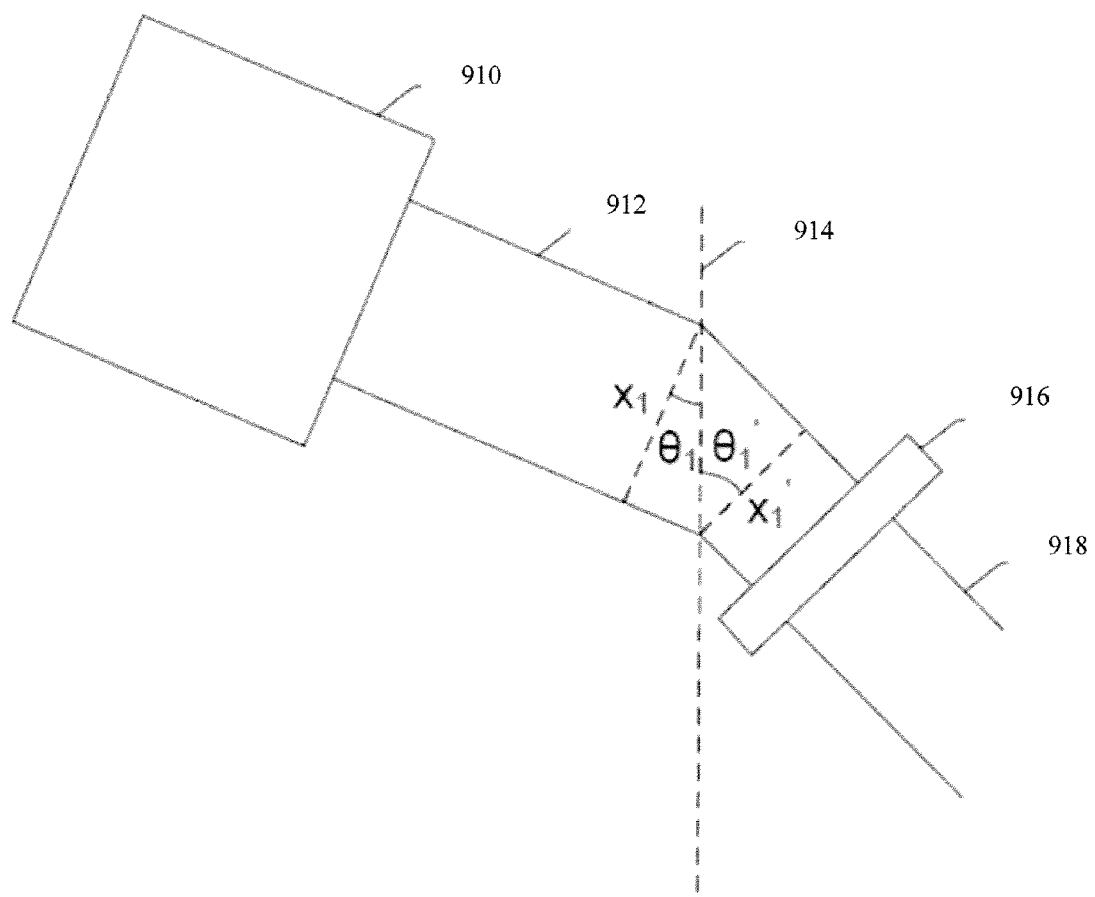
FIG. 9 illustrates an exemplary coherence reducing subsystem that may be used in combination with the sub-200 nm laser and an inspection or metrology system.

FIG. 9 illustrates aspects of a pulse-shaping or coherence reducing device used in conjunction with a pulsed laser, suitable for incorporation into an inspection or metrology system in accordance with embodiments of the present invention. A light source 910 comprises a 193 nm or sub-200 nm laser as described herein. The light source 910 generates a light beam 912 comprising a series of pulses. One aspect of this embodiment is to make use of the finite spectral range of the laser in order to perform a substantially quick temporal modulation of a light beam 912, which can be changed on approximately one-tenth-picosecond time scales (a tenth picosecond time interval is equivalent to about 1 pm in spectral width for a wavelength near 193 nm), and transform the temporal modulation to spatial modulation.

The use of a dispersive element and an electro-optic modulator is provided for speckle reduction and/or pulse shaping. For example, the illumination subsystem includes a dispersive element positioned in the path of the coherent pulses of light. As shown in FIG. 9, the dispersive element can be positioned at a plane 914 arranged at angle $\theta_1$ to the cross-section $x_1$ of the coherent pulses of light. As further shown in FIG. 9, the pulses of light exit the dispersive element at angle $\theta_1'$ and with cross-sectional dimension $x_1'$. In one embodiment, the dispersive element is a prism. In another embodiment, the dispersive element is a diffraction grating. The dispersive element is configured to reduce coherence of the pulses of light by mixing spatial and temporal characteristics of light distribution in the pulses of light. In particular, a dispersive element such as a prism or diffraction grating provides some mixing between spatial and temporal characteristics of the light distribution in the pulses of light. The dispersive element may include any suitable prism or diffraction grating, which may vary depending on the optical characteristics of the illumination subsystem and the metrology or inspection system.

The illumination subsystem further includes an electro-optic modulator positioned in the path of the pulses of light exiting the dispersive element. For example, as shown in FIG. 9, the illumination subsystem may include an electro-optic modulator 916 positioned in the path of the pulses of light exiting the dispersive element. The electro-optic modulator is configured to reduce the coherence of the pulses of light by temporally modulating the light distribution in the pulses of light. In particular, the electro-optic modulator provides an arbitrary temporal modulation of the light distribution. Therefore, the dispersive element and the electro-optic modulator have a combined effect on the pulses of light generated by the light source. In particular, the combination of the dispersive element with the electro-optic modulator creates an arbitrary temporal modulation and transforms the temporal modulation to an arbitrary spatial modulation of an output beam 918.

In one embodiment, the electro-optic modulator is configured to change the temporal modulation of the light distribution in the pulses of light at tenth picosecond time intervals. In another embodiment, the electro-optic modulator is configured to provide about 1000 aperiodic samples on each period of the modulation of the electro-optic modulator thereby providing a de-coherence time of about $10^{-13}$ seconds.

Further details of pulse-shaping and coherence and speckle reducing devices suitable for use in conjunction with a sub-200 nm laser in an inspection or metrology system can be found in U.S. Published Patent Applications 2011/0279819, entitled "ILLUMINATION SUBSYSTEMS OF A METROLOGY SYSTEM, METROLOGY SYSTEMS, AND METHODS FOR ILLUMINATING A SPECIMEN FOR METROLOGY MEASUREMENTS" which published Nov. 17, 2011, and 2011/0228263, entitled "ILLUMINATING A SPECIMEN FOR METROLOGY OR INSPEC- TION" which published Sep. 22, 2011, both by Chuang et al. Both of these applications are incorporated by reference herein.

FIGS. 10-15 illustrate systems that can include the above-described 193 nm or sub-200 nm lasers. These systems can be used in photomask, reticle, or wafer inspection applications.

In accordance with certain embodiments of the present invention, an inspection system that incorporates a 193 nm or sub-200 nm laser may simultaneously detect two channels of data on a single detector. Such an inspection system may be used to inspect a substrate such as a reticle, a photomask or a wafer, and may operate as described in U.S. Pat. No. 7,528,943 by Brown et al., which issued on May 15, 2009, and is incorporated by reference herein.

Figure 10:
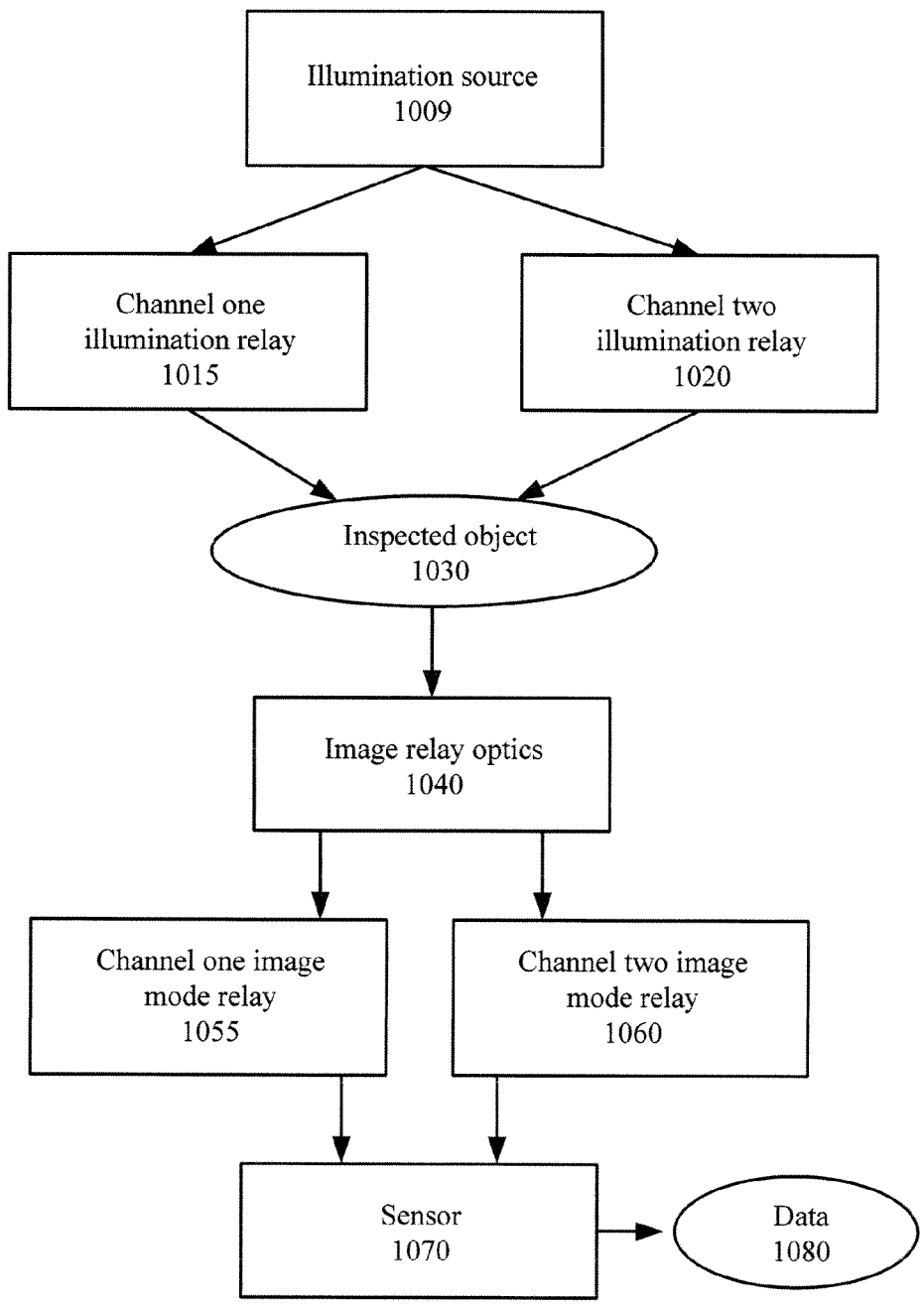
FIG. 10 illustrates an exemplary inspection system including the sub-200 nm laser.

FIG. 10 shows a reticle, photomask, or wafer inspection system 1000 that simultaneously detects two channels of image or signal on one sensor 1070. An illumination source 1009 can include a 193 nm or sub-200 nm laser as described herein. The illumination source 1009 may further comprise a pulse multiplier and/or a coherence reducing scheme. The two channels may comprise reflected and transmitted intensity when an inspected object 1030 is transparent (for example a reticle or photomask), or may comprise two different illumination modes, such as angles of incidence, polarization states, wavelength ranges, or some combination thereof.

As shown in FIG. 10, illumination relay optics 1015 and 1020 relay the illumination from illumination source 1009 to the inspected object 1030. The inspected object 1030 may be a reticle, a photomask, a semiconductor wafer, or other article to be inspected. Image relay optics 1055 and 1060 relay the light that is reflected and/or transmitted by the inspected object 1030 to the sensor 1070. The data corresponding to the detected signals or images for the two channels is shown as data 1080 and is transmitted to a computer (not shown) for processing.

Other details of reticle and photomask inspection systems and methods that may be configured to measure transmitted and reflected light from a reticle or photomask are described in U.S. Pat. No. 7,352,457 to Kvamme et al, which issued Apr. 1, 2008, and in U.S. Pat. No. 5,563,702 to Emery et al, which issued Oct. 8, 1996, both of which are incorporated by reference herein.

Figure 11:
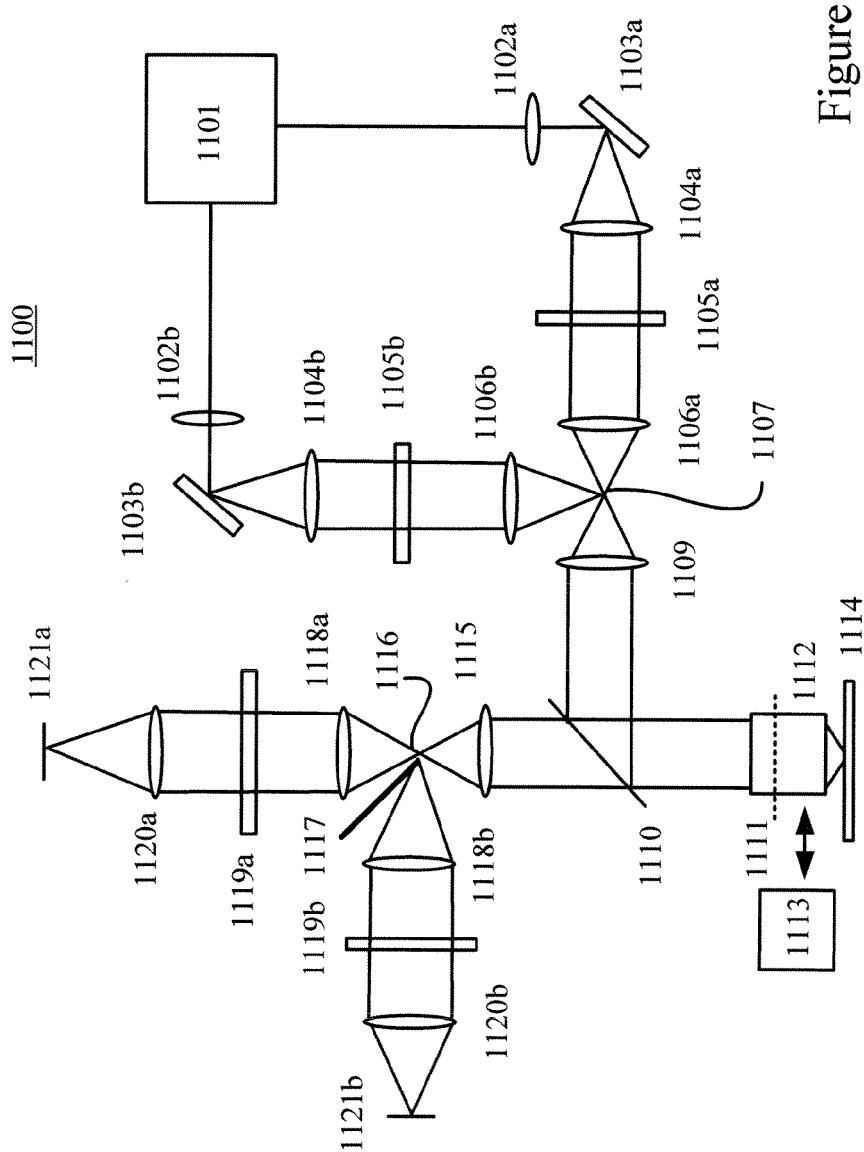
FIG. 11 illustrates an exemplary inspection system including multiple objectives and the sub-200 nm laser.

FIG. 11 illustrates an exemplary inspection system 1100 including multiple objectives and one of the above-described lasers operating at a wavelength near 193 nm, such as at wavelength between about 190 nm and 200 nm. In system 1100, illumination from a laser source 1101 is sent to multiple sections of the illumination subsystem. A first section of the illumination subsystem includes elements 1102a through 1106a. Lens 1102a focuses light from laser 1101. Light from lens 1102a then reflects from mirror 1103a. Mirror 1103a is placed at this location for the purposes of illustration, and may be positioned elsewhere. Light from mirror 1103a is then collected by lens 1104a, which forms illumination pupil plane 1105a. An aperture, filter, or other device to modify the light may be placed in pupil plane 1105a depending on the requirements of the inspection mode. Light from pupil plane 1105a then passes through lens 1106a and forms illumination field plane 1107.

A second section of the illumination subsystem includes elements 1102b through 1106b. Lens 1102b focuses light from laser 1101. Light from lens 1102b then reflects from mirror 1103b. Light from mirror 1103b is then collected by lens 1104b which forms illumination pupil plane 1105b. An aperture, filter, or other device to modify the light may be placed in pupil plane 1105b depending on the requirements of the inspection mode. Light from pupil plane 305b then passes through lens 1106b and forms illumination field plane 1107. Illumination field light energy at illumination field plane 1107 is thus comprised of the combined illumination sections.

Field plane light is then collected by lens 1109 before reflecting off beamsplitter 1110. Lenses 1106a and 1109 form an image of first illumination pupil plane 1105a at objective pupil plane 1111. Likewise, lenses 1106b and 1109 form an image of second illumination pupil plane 1105b at objective pupil plane 1111. An objective 1112 (or alternatively 1113) then takes pupil light 1111 and forms an image of illumination field 1107 at the sample 1114. Objective 1112 or 1113 can be positioned in proximity to sample 1114. Sample 1114 can move on a stage (not shown), which positions the sample in the desired location. Light reflected and scattered from the sample 1114 is collected by the high NA catadioptric objective 1112 or objective 1113. After forming a reflected light pupil at point 1111, light energy passes beamsplitter 1110 and lens 1115 before forming an internal field 1116 in the imaging subsystem. This internal imaging field is an image of sample 1114 and correspondingly illumination field 1107. This field may be spatially separated into multiple fields corresponding to the illumination fields. Each of these fields can support a separate imaging mode. For example, one imaging mode may be a bright-field imaging mode, while another may be a dark-field imaging mode.

One of these fields can be redirected using mirror 1117. The redirected light then passes through lens 1118b before forming another imaging pupil 1119b. This imaging pupil is an image of pupil 1111 and correspondingly illumination pupil 1105b. An aperture, filter, or other device to modify the light may be placed in pupil plane 1119b depending on the requirements of the inspection mode. Light from pupil plane 1119b then passes through lens 1120b and forms an image on sensor 1121b. In a similar manner, light passing by mirror or reflective surface 1117 is collected by lens 1118a and forms imaging pupil 1119a. Light from imaging pupil 1119a is then collected by lens 1120a before forming an image on detector 1121a. Light imaged on detector 1121a can be used for a different imaging mode from the light imaged on sensor 1121b.

The illumination subsystem employed in system 1100 is composed of laser source 1101, collection optics 1102-1104, beam shaping components placed in proximity to a pupil plane 1105, and relay optics 1106 and 1109. An internal field plane 1105 is located between lenses 1106 and 1109. In one preferred configuration, laser source 1101 can include one of the above-described 193 nm or sub-200 nm lasers.

With respect to laser source 1101, while illustrated as a single uniform block having two outputs, in reality this represents a laser source able to provide two channels of illumination, for example a first channel of light energy such as laser light energy at a first frequency (for example, a wavelength close to 193 nm) which passes through elements 1102a-1106a, and a second channel of light energy such as laser light energy at a second frequency (for example, a wavelength close to 234 nm) which passes through elements 1102b-1106b. Different illumination and detection modes may be employed, such as a bright-field mode in one channel and a dark-field mode in the other channel.

While light energy from laser source 1101 is shown to be emitted 90 degrees apart, and the elements 1102a-1106a and 1102b-1106b are oriented at 90 degree angles, in reality light may be emitted at various orientations, not necessarily in two dimensions, and the components may be oriented differently than as shown. FIG. 11 is therefore simply a representation of the components employed and the angles or distances shown are not to scale nor specifically required for the design.

Elements placed in proximity to pupil plane 1105 may be employed in the current system using the concept of aperture shaping. Using this design, uniform illumination or near uniform illumination may be realized, as well as individual point illumination, ring illumination, quadrapole illumination, or other desirable patterns.

Various implementations for the objectives may be employed in a general imaging subsystem. A single fixed objective may be used. The single objective may support all the desired imaging and inspection modes. Such a design is achievable if the imaging system supports a relatively large field size and relatively high numerical aperture. The numerical aperture can be reduced to a desired value by using internal apertures placed at the pupil planes 1105a, 1105b, 1119a, and 1119b.

Multiple objectives may also be used. For example, although two objectives 1112 and 1113 are shown, any number is possible. Each objective in such a design may be optimized for each wavelength produced by laser source 1101. These objectives can either have fixed positions or be moved into position in proximity to the sample 1114. To move multiple objectives in proximity to the sample, rotary turrets may be used as are common on standard microscopes. Other designs for moving objectives in proximity of a sample are available, including but not limited to translating the objectives laterally on a stage, and translating the objectives on an arc using a goniometer. In addition, any combination of fixed objectives and multiple objectives on a turret can be achieved in accordance with the present system.

The maximum numerical apertures of the current embodiments approach or exceed 0.97, but may in certain instances be smaller. The wide range of illumination and collection angles possible with this high NA catadioptric imaging system, combined with its large field size allows the system to simultaneously support multiple inspection modes. As may be appreciated from the previous paragraphs, multiple imaging modes can be implemented using a single optical system or machine in connection with the illumination device. The high NA disclosed for illumination and collection permits the implementation of imaging modes using the same optical system, thereby allowing optimization of imaging for different types of defects or samples.

The imaging subsystem also includes intermediate image forming optics 1115. The purpose of the image forming optics 1115 is to form an internal image 1116 of the sample 1114. At this internal image 1116, a mirror 1117 can be placed to redirect light corresponding to one of the inspection modes. It is possible to redirect the light at this location because the light for the imaging modes are spatially separate. The image forming optics 1118 and 1120 can be implemented in several different forms including a varifocal zoom, multiple afocal tube lenses with focusing optics, or multiple image forming mag tubes. U.S. Published Patent Application 2009/0180176, which published on Jul. 16, 2009 and is incorporated by reference herein, describes additional details of system 1100.

Figure 12:
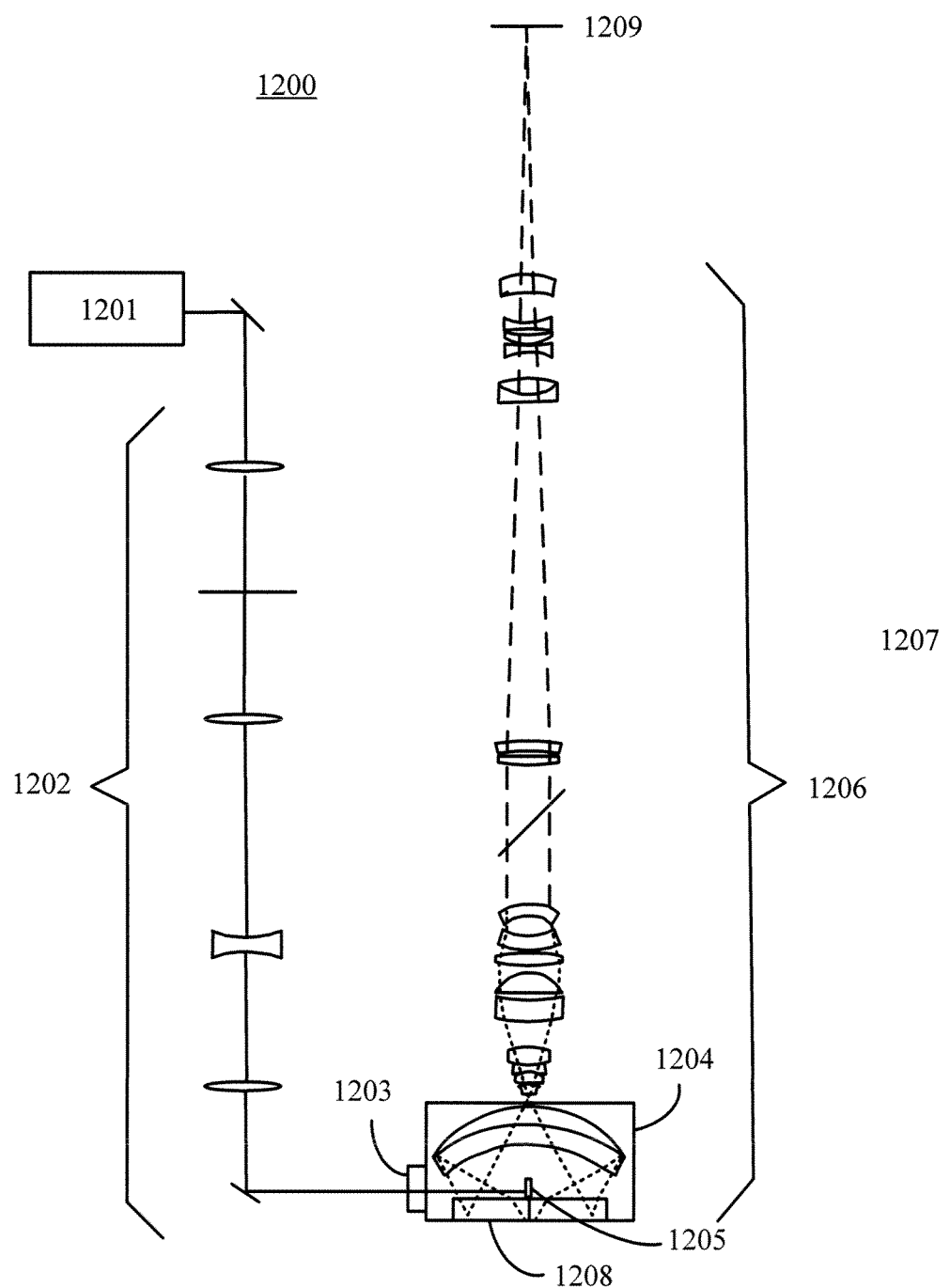
FIG. 12 illustrates an exemplary inspection system with dark-field and bright-field modes and including the sub-200 nm laser.

FIG. 12 illustrates the addition of a normal incidence laser dark-field illumination to a catadioptric imaging system 1200. The dark-field illumination includes a sub-200 nm laser 1201, adaptation optics 1202 to control the illumination beam size and profile on the surface being inspected, an aperture and window 1203 in a mechanical housing 1204, and a prism 1205 to redirect the laser along the optical axis at normal incidence to the surface of a sample 1208. Prism 1205 also directs the specular reflection from surface features of sample 1208 and reflections from the optical surfaces of an objective 1206 along the optical path to an image plane 1209. Lenses for objective 1206 can be provided in the general form of a catadioptric objective, a focusing lens group, and a zooming tube lens section (see U.S. Pat. No. 5,999,310, which issued on Dec. 7, 1999 and is incorporated by reference herein). In a preferred embodiment, laser 1201 can include the above-described 193 nm or sub-200 nm laser. In some embodiments, the laser 1201 may further include the above described pulse multiplier and/or the above described coherence reducer. U.S. Published Patent Application 2007/0002465, which published on Jan. 4, 2007 and is incorporated by reference herein, describes system 1200 in further detail.

Figure 13A:
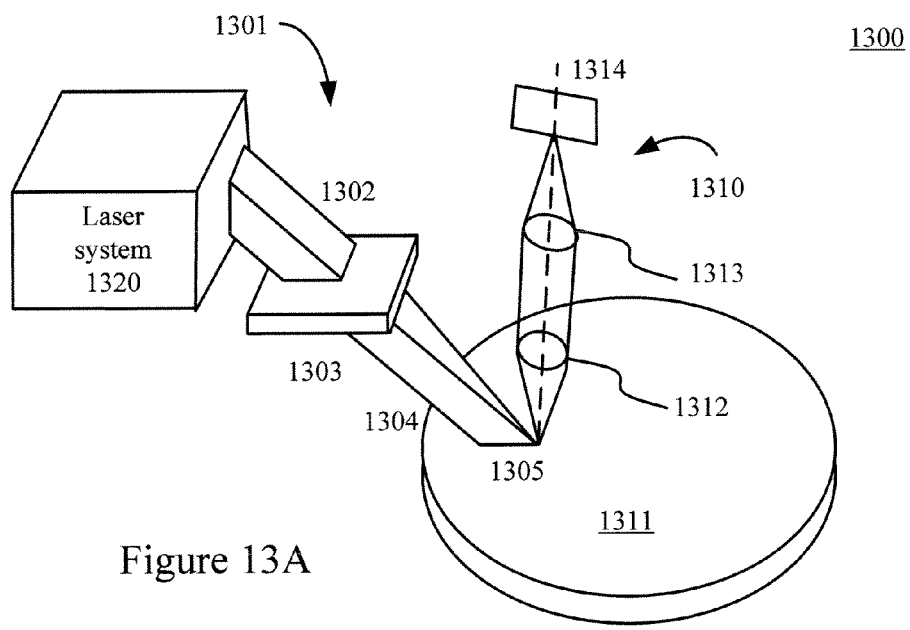
FIGS. 13A and 13B illustrate an exemplary dark-field patterned-wafer inspection system including the sub-200 nm laser.

FIG. 13A illustrates a surface inspection apparatus 1300 that includes illumination system 1301 and collection system 1310 for inspecting areas of surface 1311. As shown in FIG. 13A, a laser system 1320 directs a light beam 1302 through a lens 1303. In a preferred embodiment, laser system 1320 includes the above-described sub-200 nm laser, an annealed crystal, and a housing to maintain the annealed condition of the crystal. First beam shaping optics can be configured to receive a beam from the laser and focus the beam to an elliptical cross section at a beam waist in or proximate to the crystal.

Lens 1303 is oriented so that its principal plane is substantially parallel to a sample surface 1311 and, as a result, illumination line 1305 is formed on surface 1311 in the focal plane of lens 1303. In addition, light beam 1302 and focused beam 1304 are directed at a non-orthogonal angle of incidence to surface 1311. In particular, light beam 1302 and focused beam 1304 may be directed at an angle between about 1 degree and about 85 degrees from a normal direction to surface 1311. In this manner, illumination line 1305 is substantially in the plane of incidence of focused beam 1304.

Collection system 1310 includes lens 1312 for collecting light scattered from illumination line 1305 and lens 1313 for focusing the light coming out of lens 1312 onto a device, such as charge coupled device (CCD) or CMOS sensor 1314, comprising an array of light sensitive detectors. In one embodiment, sensor 1314 may include a linear array of detectors. In such cases, the linear array of detectors within CCD or CMOS sensor 1314 can be oriented parallel to illumination line 1315. In one embodiment, multiple collection systems can be included, wherein each of the collection systems includes similar components, but differ in orientation.

Figure 13B:
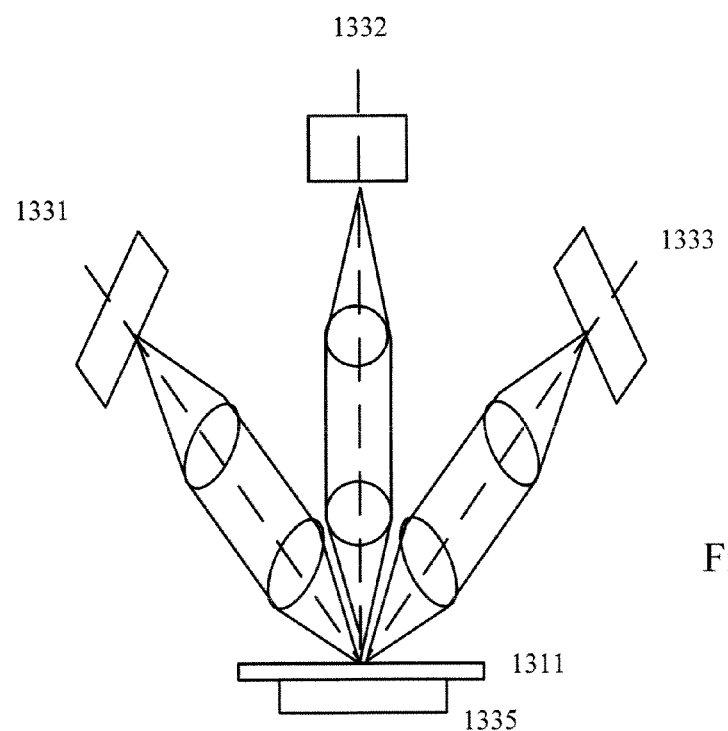

For example, FIG. 13B illustrates an exemplary array of collection systems 1331, 1332, and 1333 for a surface inspection apparatus (wherein its illumination system, e.g. similar to that of illumination system 1301, is not shown for simplicity). First optics in collection system 1331 can collect a first beam of radiation along a first path from a line on the surface of sample 1311. Second optics in collection system 1332 can collect a second beam of radiation along a second path from the same line on the surface of sample 1311. Third optics in collection system 1333 can collect a third beam of radiation along a third path from the same line on the surface of sample 1311. Note that the first, second, and third paths are at different angles of incidence to said surface of sample 1311. A platform 1335 supporting sample 1311 can be used to cause relative motion between the multiple beams and sample 1311 so that the line is scanned across the surface of sample 1311. U.S. Pat. No. 7,525,649, which issued on Apr. 28, 2009 and is incorporated by reference herein, describes surface inspection apparatus 1300 and other multiple collection systems in further detail.

Figure 14:
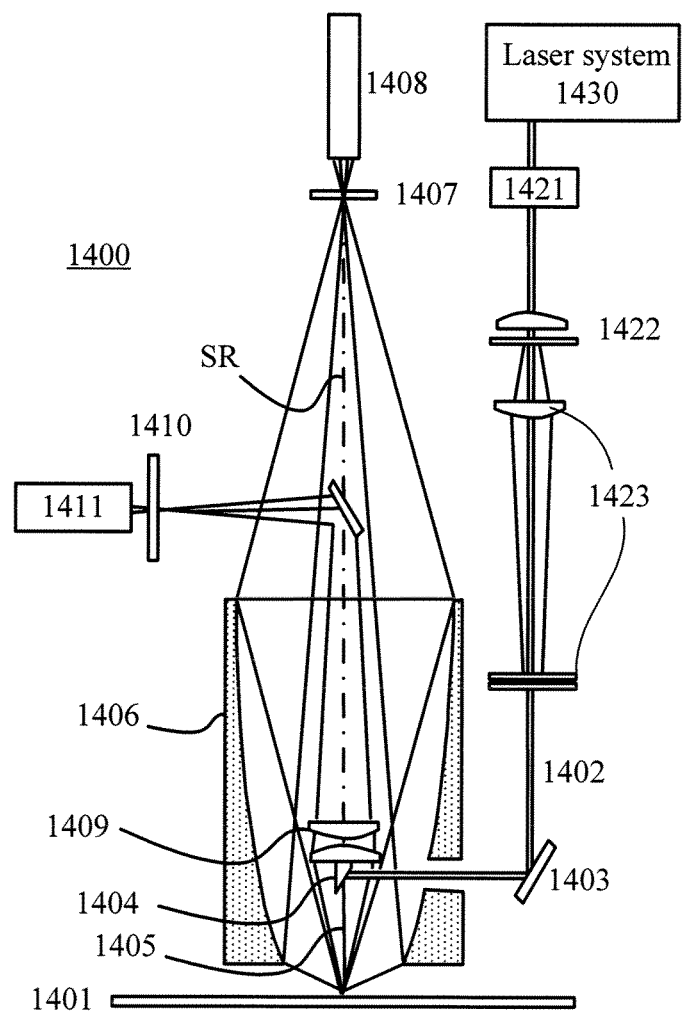
FIG. 14 illustrates an exemplary unpatterned-wafer inspection system including the sub-200 nm laser.

FIG. 14 illustrates an exemplary surface inspection system 1400 that can be used for inspecting anomalies on a surface 1401. In this embodiment, surface 1401 can be illuminated by a substantially stationary illumination device portion of a laser system 1430 comprising a laser beam generated by the above-described 193 nm or sub-200 nm laser. The output of laser system 1430 can be consecutively passed through polarizing optics 1421, a beam expander and aperture 1422, and beam-forming optics 1423 to expand and focus the beam.

The focused laser beam 1402 is then reflected by a beam folding component 1403 and a beam deflector 1404 to direct the beam 1405 towards surface 1401 for illuminating the surface. In the preferred embodiment, beam 1405 is substantially normal or perpendicular to surface 1401, although in other embodiments beam 1405 may be at an oblique angle to surface 1401.

In one embodiment, beam 1405 is substantially perpendicular or normal to surface 1401 and beam deflector 1404 reflects the specular reflection of the beam from surface 1401 towards beam turning component 1403, thereby acting as a shield to prevent the specular reflection from reaching the detectors. The direction of the specular reflection is along line SR, which is normal to the surface 1401 of the sample. In one embodiment where beam 1405 is normal to surface 1401, this line SR coincides with the direction of illuminating beam 1405, where this common reference line or direction is referred to herein as the axis of inspection system 1400. Where beam 1405 is at an oblique angle to surface 1401, the direction of specular reflection SR would not coincide with the incoming direction of beam 1405; in such instance, the line SR indicating the direction of the surface normal is referred to as the principal axis of the collection portion of inspection system 1400.

Light scattered by small particles is collected by mirror 1406 and directed towards aperture 1407 and detector 1408. Light scattered by large particles is collected by lenses 1409 and directed towards aperture 1410 and detector 1411. Note that some large particles will scatter light that is also collected and directed to detector 1407, and similarly some small particles will scatter light that is also collected and directed to detector 1411, but such light is of relatively low intensity compared to the intensity of scattered light the respective detector is designed to detect. In one embodiment, detector 1411 can include an array of light sensitive elements, wherein each light sensitive element of the array of light sensitive elements is configured to detect a corresponding portion of a magnified image of the illumination line. In one embodiment, inspection system 1400 can be configured for use in detecting defects on unpatterned wafers. U.S. Pat. No. 6,271,916, which issued on Aug. 7, 2011 and is incorporated by reference herein, describes inspection system 1400 in further detail.

Figure 15:
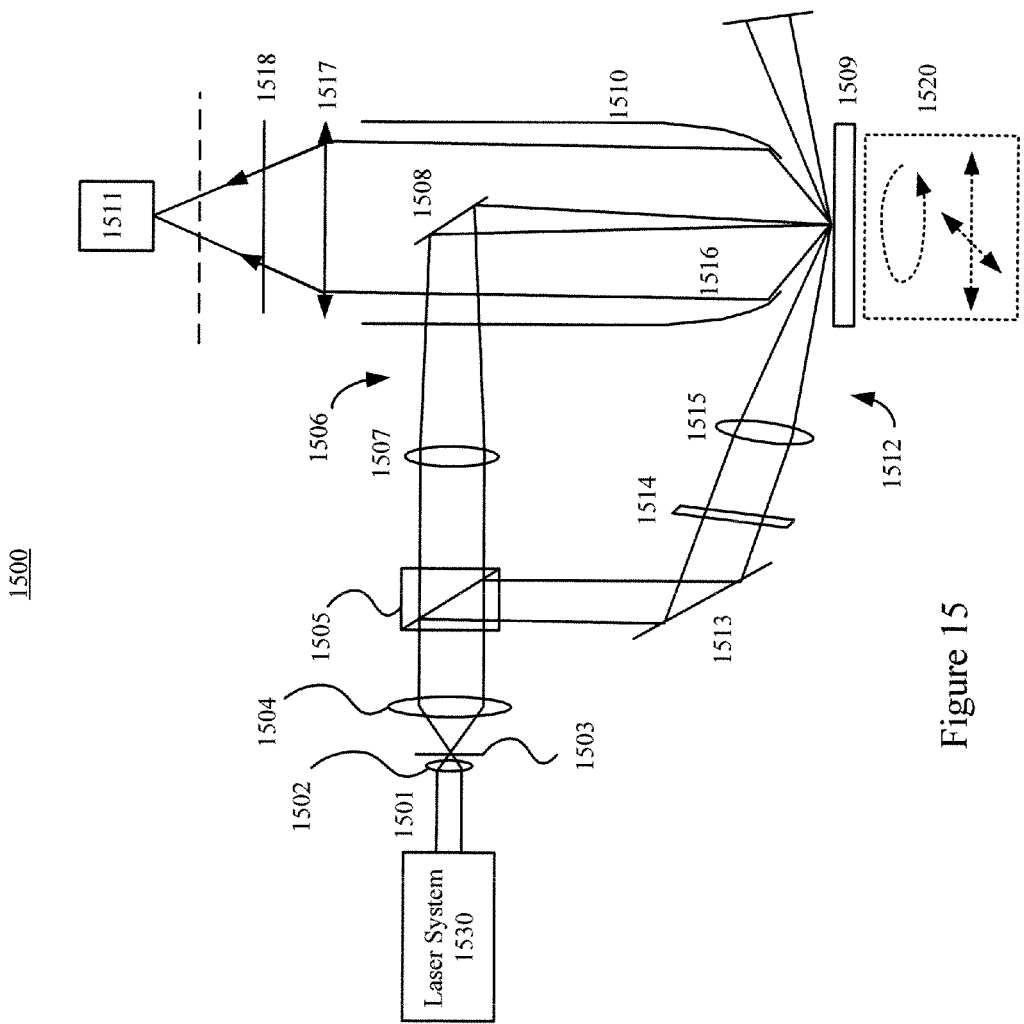
FIG. 15 illustrates another exemplary unpatterned-wafer inspection system including the sub-200 nm laser.

FIG. 15 illustrates another exemplary inspection system 1500 configured to implement anomaly detection using both normal and oblique illumination beams. In this configuration, a laser system 1530, which includes the above-described sub-200 nm laser, can provide a laser beam 1501. A lens 1502 focuses the beam 1501 through a spatial filter 1503 and lens 1504 collimates the beam and conveys it to a polarizing beam splitter 1505. Beam splitter 1505 passes a first polarized component to the normal illumination channel and a second polarized component to the oblique illumination channel, where the first and second components are orthogonal. In the normal illumination channel 1506, the first polarized component is focused by optics 1507 and reflected by mirror 1508 towards a surface of a sample 1509. The radiation scattered by sample 1509 is collected and focused by a paraboloidal mirror 1510 to a photomultiplier tube or detector 1511.

In the oblique illumination channel 1512, the second polarized component is reflected by beam splitter 1505 to a mirror 1513 which reflects such beam through a half-wave plate 1514 and focused by optics 1515 to sample 1509. Radiation originating from the oblique illumination beam in the oblique channel 1512 and scattered by sample 1509 is collected by paraboloidal mirror 1510 and focused to photomultiplier tube 1511. Photomultiplier tube 1511 has a pinhole entrance. The pinhole and the illuminated spot (from the normal and oblique illumination channels on surface 1509) are preferably at the foci of the paraboloidal mirror 1510.

The paraboloidal mirror 1510 collimates the scattered radiation from sample 1509 into a collimated beam 1516. Collimated beam 1516 is then focused by an objective 1517 and through an analyzer 1518 to the photomultiplier tube 1511. Note that curved mirrored surfaces having shapes other than paraboloidal shapes may also be used. An instrument 1520 can provide relative motion between the beams and sample 1509 so that spots are scanned across the surface of sample 1509. U.S. Pat. No. 6,201,601, which issued on Mar. 13, 2001 and is incorporated by reference herein, describes inspection system 1500 in further detail.

The most critical frequency conversion step of a deep-UV laser is the final conversion stage. In the above-described lasers, this final conversion stage mixes a wavelength of approximately 1109 nm with one of approximately 234 nm. CLBO enables the use of substantially non-critical phase matching for that final frequency conversion with a phase matching angle of approximately 85° at a temperature of approximately 80-120° C. Near non-critical phase matching is more efficient and more stable than critical phase matching because the low walk-off angle (approximately 7-9 mrad) allows a longer crystal to be used. Near non-critical phase matching is also less affected by small changes in alignment than critical phase matching. Note that the longer crystal also allows the use of lower peak power densities in the crystal while maintaining the same overall conversion efficiency, thereby slowing damage accumulation to the crystal. Notably, mixing wavelengths of approximately 1109 nm and approximately 234 nm is more efficient than $8^{th}$ harmonic generation. Therefore, the above-described 193 nm and sub-200 nm lasers can provide significant system advantages for photomask, reticle, or wafer inspection.

The various embodiments of the structures and methods of this invention that are described above are illustrative only of the principles of this invention and are not intended to limit the scope of the invention to the particular embodiments described. For example, non-linear crystals other than those listed above can be used for some of the frequency conversion stages. Thus, the invention is limited only by the following claims and their equivalents.

The invention claimed is:

1. An optical inspection system for inspecting a surface of a photomask, reticle, or semiconductor wafer for defects, the system comprising:
   a light source for emitting an incident light beam, the light source including a frequency mixing stage for combining light at a wavelength of approximately 1109 nm with light at a wavelength of approximately 234 nm to generate light at a wavelength between 190 nm and 200 nm;

an optical system including a plurality of optical components for directing the incident light beam to a surface of the photomask, reticle or semiconductor wafer;

optics for collecting at least two channels of light reflected or transmitted from the photomask, reticle or semiconductor wafer, and relaying that light to a sensor; and a sensor that simultaneously detects the at least two channels of light, wherein the optics further comprises at least one electro-optic modulator to reduce a coherence of the light at a wavelength between 190 nm and 200 nm.

2. An optical inspection system for inspecting a surface of a photomask, reticle, or semiconductor wafer for defects, the system comprising:

a light source for emitting an incident light beam, the light source including a frequency mixing stage for combining light at a wavelength of approximately 1109 nm with light at a wavelength of approximately 234 nm to generate light at a wavelength between 190 nm and 200 nm;

an optical system including a plurality of optical components for directing the incident light beam to a surface of the photomask, reticle or semiconductor wafer;

optics for collecting at least two channels of light reflected or transmitted from the photomask, reticle or semiconductor wafer, and relaying that light to a sensor; and a sensor that simultaneously detects the at least two channels of light, wherein the at least two channels include light reflected from the surface of the photomask, reticle or semiconductor wafers, and light transmitted through the photomask, reticle or semiconductor wafer.

3. An inspection system for inspecting a surface of a sample, the inspection system comprising:

an illumination subsystem configured to produce a plurality of channels of light, each channel of light produced having differing characteristics from at least one other channel of light energy, the illumination subsystem including a frequency mixing stage for combining light at a wavelength of approximately 1109 nm with light at a wavelength of approximately 234 nm to generate light at a wavelength between 190 nm and 200 nm for at least one channel;

optics configured to receive the plurality of channels of light and combine the plurality of channels of light energy into a spatially separated combined light beam and direct the spatially separated combined light beam toward the sample; and a data acquisition subsystem comprising at least one detector configured to detect reflected light from the sample, wherein the data acquisition subsystem is configured to separate the reflected light into a plurality of received channels corresponding to the plurality of channels of light.

* * * * *